United States Patent [19]

Danilewicz et al.

[11] Patent Number: 5,750,520
[45] Date of Patent: May 12, 1998

[54] ANTITHROMBOTIC AMIDINOPHENYLALANINE AND AMIDINOPYRIDYLALANINE DERIVATIVES

[75] Inventors: John Christopher Danilewicz; David Ellis; Ryszard Jurek Kobylecki, all of Sandwich, United Kingdom

[73] Assignee: Pfizer Inc., New York, N.Y.

[21] Appl. No.: 628,642

[22] PCT Filed: Oct. 24, 1994

[86] PCT No.: PCT/EP94/03509

§ 371 Date: Apr. 19, 1996

§ 102(e) Date: Apr. 19, 1996

[87] PCT Pub. No.: WO95/13274

PCT Pub. Date: May 18, 1995

[30] Foreign Application Priority Data

Nov. 8, 1993 [GB] United Kingdom ............... 9322976

[51] Int. Cl.$^6$ ............... C07D 401/12; C07D 217/00; C07D 217/16; A61K 31/55

[52] U.S. Cl. ............... 514/212; 514/307; 540/597; 546/145

[58] Field of Search ............... 546/145; 540/597; 514/212, 307

[56] References Cited

U.S. PATENT DOCUMENTS 5,518,735  5/1996  Sturzebecher ............... 424/449

FOREIGN PATENT DOCUMENTS 9208709  5/1992  WIPO.

OTHER PUBLICATIONS

Wagner, G. et al., Pharmazie, 36, 9, pp. 597–603 (1981).
Wagner, G. et al., Pharmazie, 39, 4, pp. 226–230 (1984).

*Primary Examiner*—Mukund J. Shah
*Assistant Examiner*—Deepak R. Rao
*Attorney, Agent, or Firm*—Peter C. Richardson; Gregg C. Benson; Robert T. Ronau

[57] ABSTRACT

This invention relates to compounds of formula (I),

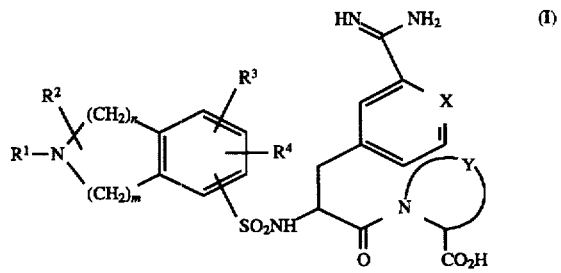

pharmaceutically acceptable salt thereof, and pharmaceutically acceptable solvates of either entity, wherein X is CH or N; Y is optionally monounsaturated $C_3$-$C_5$ alkylene optionally substituted with $C_1$-$C_4$ alkyl or methylene; $R^1$ is H; $C_1$-$C_4$ alkyl optionally substituted with $C_1$-$C_4$ alkoxy, OH, $NR^5R^6$, $CONR^5R^6$, $C_3$-$C_6$ cycloalkyl or aryl; or $C_3$-$C_6$ alkenyl; $R^2$ is H; $C_1$-$C_4$ alkyl optionally substituted with $C_1$-$C_4$ alkoxy, OH, $NR^5R^6$, $CONR^5R^6$, $C_3$-$C_6$ cycloalkyl or aryl; or $CONR^5R^6$; $R^3$ and $R^4$ are each independently selected from H; $C_1$-$C_4$ alkyl optionally substituted with $NR^5R^6$; $C_1$-$C_4$ alkoxy; halo; $CONR^5R^6$ and aryl; $R^5$ and $R^6$ are each independently selected from H and $C_1$-$C_4$ alkyl; and m and n are each independently 1, 2 or 3; are potent and selective thrombin inhibitors useful in the treatment of, inter alia, deep vein thrombosis; reocclusion following thrombolytic therapy; chronic arterial obstruction; peripheral vascular disease; acute myocardial infarction; unstable angina; atrial fibrillation; thrombotic stroke; transient ischaemic attacks; restenosis and occlusion following angioplasty; or neurodegenerative disorders.

18 Claims, No Drawings

ANTITHROMBOTIC AMIDINOPHENYLALANINE AND AMIDINOPYRIDYLALANINE DERIVATIVES

CROSS-REFERENCE TO RELATED APPLICATIONS

This is the national stage under 35 U.S.C. §371 of International Patent Application No. PCT/EP94/03509, filed Oct. 24, 1994, claiming priority to Great Britain patent application No. 9322976.3, filed Nov. 8, 1993.

This invention relates to a series of amidinophenylalanine and amidinopyridylalanine derivatives, which are antithrombotic agents, having utility in a variety of therapeutic areas including the prevention and/or treatment of deep vein thrombosis (DVT) after surgery, major medical illness, paralysis, malignancy, prolonged immobilisation trauma, application of lower limb plaster casts, or fractures of the lower limbs or pelvis; recurrent DVT; DVT during pregnancy when there is a previous history thereof; reocclusion following thrombolytic therapy; chronic arterial obstruction; peripheral vascular disease; acute myocardial infarction; unstable angina; atrial fibrillation; thrombotic stroke; transient ischaemic attacks; disseminated intravascular coagulation; coagulation in extra-corporeal circuits; occlusion of arterio-venous shunts and blood vessel grafts (including coronary artery by-pass-grafts); and restenosis and occlusion following angioplasty. They also have utility as an adjunct to thrombolytic therapy.

The compounds of the invention are potent and selective inhibitors of thrombin, which is the final serine protease enzyme in the coagulation cascade. The prime function of thrombin is the cleavage of fibrinogen to produce fibrin which forms linear insoluble polymers which, in turn, are cross-linked by factor XIIIa, itself activated by thrombin. In addition, thrombin regulates its own production by activation of factors V and VIII earlier in the cascade. It also has important actions at the cellular level, where it acts on specific receptors to cause platelet aggregation, endothelial cell activation and fibroblast proliferation. Thus thrombin has a central regulatory role in homeostasis and thrombus formation.

Clearly then, potent, selective and orally bioavailable thrombin inhibitors represent an attractive target for the convenient therapeutic control of thrombosis. In addition, thrombin potently causes neurite retraction and therefore a thrombin inhibitor is of potential therapeutic utility in the treatment of acute and chronic neurodegenerative disorders. Furthermore, the compounds disclosed herein are of potential value in the treatment of inflammatory disorders and scarring, and in wound healing.

Because of their potential as substrate mimics, arginine derivatives have been explored as thrombin inhibitors and this work led to the discovery of argatroban (see Cardiovascular Drug Rev., 1991, 9, 247). In turn, other research groups have sought to express the basic arginine function in a variety of alternative structures; for example, WO-A-92/08709 discloses amidino, guanidino, amidoximino, aminomethyl and amino phenylalanine derivatives as antithrombotic agents.

The compounds of the present invention are significantly more potent thrombin inhibitors than those mentioned above, selective (in comparison with their inhibition of, for example, trypsin, plasmin, butyrylcholinesterase and elastase), well tolerated and orally bioavailable.

Accordingly, the present invention provides a compound of formula (I):

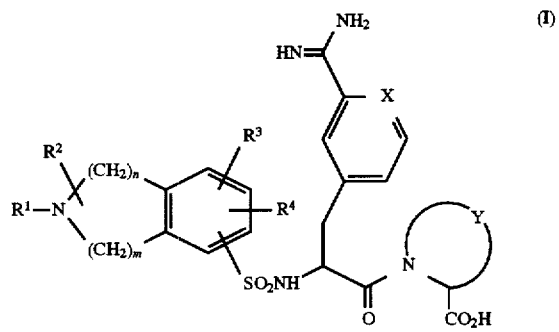

pharmaceutically acceptable salts thereof, and pharmaceutically acceptable solvates of either entity, wherein X is CH or N;

Y is optionally monounsaturated $C_3$-$C_5$ alkylene optionally substituted with $C_1$-$C_4$ alkyl or methylene;

$R^1$ is H; $C_1$-$C_4$ alkyl optionally substituted with $C_1$-$C_4$ alkoxy, OH, $NR^5R^6$, $CONR^5R^6$, $C_3$-$C_6$ cycloalkyl or aryl; or $C_3$-$C_6$ alkenyl;

$R^2$ is H; $C_1$-$C_4$ alkyl optionally substituted with $C_1$-$C_4$ alkoxy, OH, $NR^5R^6$, $CONR^5R^6$, $C_3$-$C_6$ cycloalkyl or aryl; or $CONR^5R^6$;

$R^3$ and $R^4$ are each independently selected from H; $C_1$-$C_4$ alkyl optionally substituted with $NR^5R^6$; $C_1$-$C_4$ alkoxy; halo; $CONR^5R^6$ and aryl;

$R^5$ and $R^6$ are each independently selected from H and $C_1$-$C_4$ alkyl; and m and n are each independently 1, 2 or 3.

In the above definition, aryl means phenyl optionally substituted with one, two or three substituents independently selected from $C_1$-$C_4$ alkyl, $C_1$-$C_4$ alkoxy, OH, halo and $CF_3$; halo means fluoro, chloro, bromo or iodo. Unless otherwise indicated, alkyl and alkoxy groups having three or more carbon atoms and alkenyl groups having four or more carbon atoms may be straight-chain or branched-chain.

The compounds of formula (I) contain two or more asymmetric centres and thus can exist as stereoisomers, i.e. as enantiomers or as diastereoisomers, and the invention includes both the separated individual stereoisomers as well as mixtures thereof.

The preferred stereoisomers are of formula (IA):

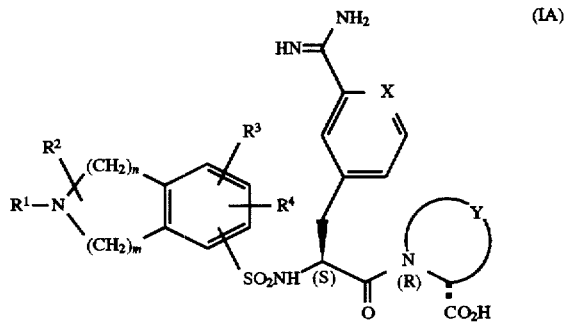

Also included in the invention are radiolabelled derivatives of compounds of formula (I) which are suitable for biological studies.

The pharmaceutically acceptable salts of the compounds of formula (I) are, for example, non-toxic acid addition salts formed with inorganic acids such as hydrochloric, hydrobromic, sulphuric and phosphoric acid, with organo-carboxylic acids, or with organo-sulphonic acids. Compounds of formula (I) can also provide pharmaceutically acceptable metal salts, in particular non-toxic alkali metal salts, with bases. Examples include the sodium and potassium salts.

A preferred group of compounds of formula (I) is that wherein Y is monounsaturated $C_3$-$C_5$ alkylene substituted with methyl or ethyl; $R^1$ is H; or $C_1$-$C_4$ alkyl optionally substituted with $NR^5R^6$ or phenyl; $R^2$ is H; $C_1$-$C_2$ alkyl substituted with $C_1$-$C_4$ alkoxy, $NR^5R^6$ or $CONR^5R^6$; or $CONR^5R^6$; $R^3$ and $R^4$ are each independently selected from H, methyl, $CH_2NR^5R^6$, methoxy, $CONR^5R^6$ and phenyl; $R^5$ and $R^6$ are each independently selected from H and methyl; and X, m and n are as previously defined for formula (I).

A more preferred group of compounds is that of formula (IB):

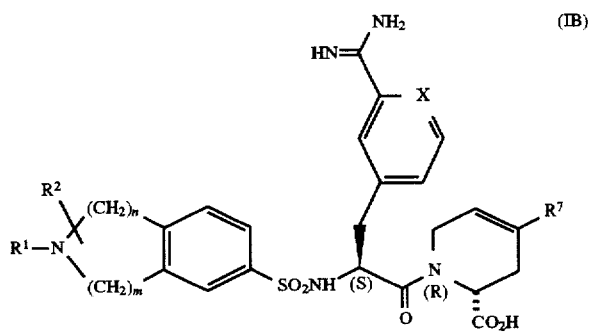

wherein $R^1$ is methyl, ethyl, 2-propyl, 3-dimethylamino-1-propyl or benzyl; $R^2$ is H, $CH_2OCH_3$ or $CH_2CON(CH_3)_2$; $R^7$ is methyl or ethyl; m is 1 or 2; n is 1 or 2; and X is as previously defined for formula (I).

Particularly preferred individual compounds of the invention include:

4-methyl-1-[N-(2-methyl-1,2,3,4-tetrahydroisoquinoline-7-sulphonyl)-3-amidino-(S)-phenylalanyl]-1,2,3,6-tetrahydropyridine-2(R)-carboxylic acid;

4-methyl-1-[N-(3-methyl-2,3,4,5-tetrahydro-1l-3-benzazepine-7-sulphonyl)-3-amidino-(S)-phenylalanyl]-1,2,3,6-tetrahydropyridine-2(R)-carboxylic acid; and 1-{N-[3-(3)-dimethylamino-1-propyl)-2,3,4,5-tetrahydro-1H-3-benzazepine-7-sulphonyl]-3-amidino-(S)-phenylalanyl}-4-methyl-1,2,3,6-tetrahydropyridine-2(R)-carboxylic acid;

and pharmaceutically acceptable salts thereof, and pharmaceutically acceptable solvates of either entity.

In another aspect, the present invention provides processes for the preparation of compounds of formula (I) and their pharmaceutically acceptable salts.

A compound of formula (I) may be prepared by hydrolysis of its lower alkyl ester precursor of formula (II):

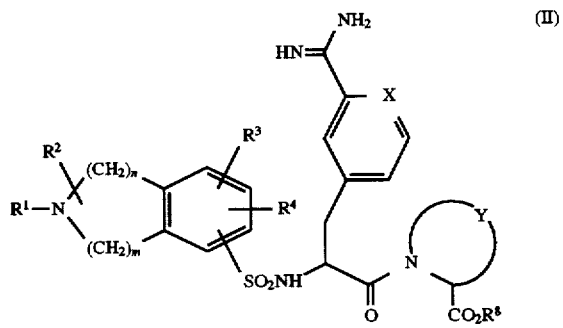

wherein $R^8$ is $C_1$-$C_3$ alkyl, preferably methyl or ethyl, and X, Y, $R^1$, $R^2$, $R^3$, $R^4$, m and n are as previously defined for formula (I).

The reaction may be acid- or base-catalysed, but is generally carried out using an alkali metal hydroxide such as sodium or potassium hydroxide in aqueous solution, optionally in the presence of a suitable cosolvent, at from about room temperature to about 100° C. Preferred conditions are the use of aqueous sodium hydroxide solution, with 1,4-dioxan as cosolvent, at about room temperature.

The novel intermediate esters of formula (II) also form part of the invention.

A compound of formula (II) may be prepared from a compound of formula (III):

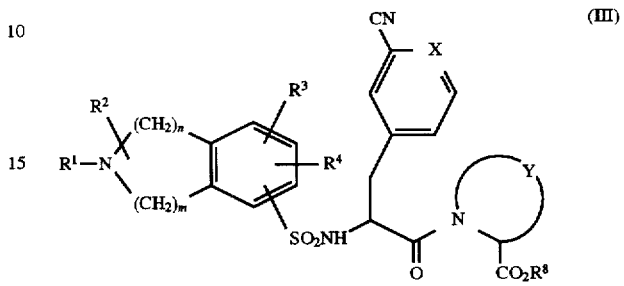

wherein X, Y, $R^1$, $R^2$, $R^3$, $R^4$, $R^8$, m and n are as previously defined for formula (II).

This may be achieved by conversion of the nitrile group to the required amidine via an intermediate imino ether under conventional conditions. For example, a solution of the nitrile in a lower alkanol such as methanol or ethanol is saturated with hydrogen chloride at about 0° C. to generate the imino ether hydrochloride which, in turn, is treated as a solution in the same alcohol with excess ammonia at from about −10° to about 0° C. followed by heating of the resulting mixture under reflux.

In the case where the saturation with ammonia step is effected under reflux, a compound of formula (III) wherein $R^1$ is a protecting group ($P^1$) which is susceptible to removal under such conditions, e.g. trifluoroacetyl, will provide a compound of formula (II) wherein $R^1$ is H.

Alternatively, the imino ether free base may be generated in situ by treatment of the nitrile with the appropriate alkali metal alkoxide in the corresponding lower alkanol as solvent at about room temperature; for example, sodium methoxide or sodium ethoxide in methanol or ethanol respectively. This step is followed by treatment of the imino ether solution with a suitable ammonium salt, e.g. ammonium chloride, at about room temperature.

A compound of formula (III) may be prepared by a variety of methods, one of which is N-alkylation of a compound of formula (IV):

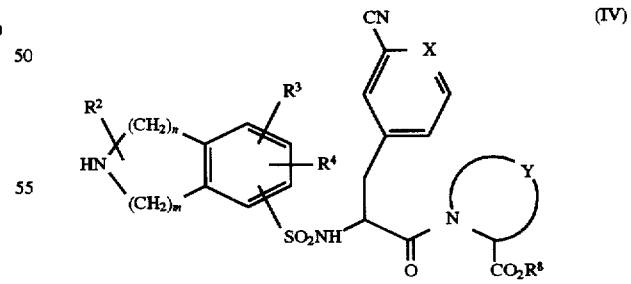

wherein X, Y, $R^2$, $R^3$, $R^4$, $R^8$, m and n are as previously defined for formula (III), with the proviso that none of the other nucleophilic centres within (IV) provides a more reactive alkylation site, e.g. in certain cases where $R^2$, $R^3$ or $R^4$ is $C_1$-$C_4$ alkyl substituted with $NR^5R^6$.

In general, the alkylation may be achieved by reaction of a compound of formula (IV) with a compound of formula $R^1Q$, wherein $R^1$ is as previously defined for formula (III)

and Q is a suitable leaving group, e.g. halo, $C_1$-$C_4$ alkanesulphonyloxy, trifluoromethanesulphonyloxy or arylsulphonyloxy (such as benzenesulphonyloxy or R-toluenesulphonyloxy), in the presence of an appropriate base, e.g. the carbonate or bicarbonate salt of an alkali or alkaline earth metal, in a suitable solvent such as a $C_1$-$C_3$ alkanol, acetonitrile, dimethylformamide or N,N-dimethylacetamide, optionally in the presence of the iodide salt of sodium or potassium, at from about room temperature to about 100° C. Preferably Q is chloro, bromo or iodo, the base is sodium or potassium carbonate or bicarbonate, the solvent is acetonitrile and the reaction is conducted at about 80°–85° C.

When $R^1$ is methyl, the N-methylation can be conveniently carried out by a reductive alkylation procedure wherein (IV) is treated with aqueous formaldehyde solution followed by an appropriate reducing agent in a suitable solvent. Preferably both reaction steps are conducted at room temperature in dichloromethane as solvent, with sodium triacetoxyborohydride being employed in the reduction step.

Alternatively, a compound of formula (III) may be prepared by coupling a compound of formula (V):

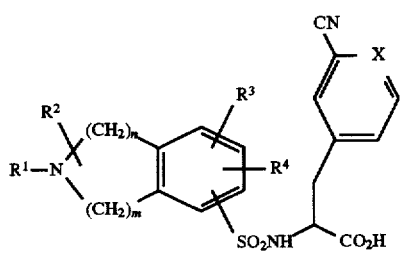

wherein X, $R^1$, $R^2$, $R^3$, $R^4$, m and n are as previously defined for formula (III), with a compound of formula (VI):

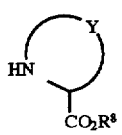

wherein Y and $R^8$ are as previously defined for formula (III). The coupling reaction may be achieved using conventional amide bond-forming techniques. For example, the acid may be activated by formation of the corresponding acyl halide, e.g. bromide or chloride, followed by reaction of the latter with an amine of formula (VI), optionally in the presence of a reaction-inert base to act as acid scavenger, in a suitable solvent such as dichloromethane. Alternatively, any of a host of peptide coupling variations may be used. For example, the acid may be activated using a carbodiimide such as 1,3-dicyclohexylcarbodiimide or 1-ethyl-3-dimethylaminopropylcarbodiimide, optionally in the presence of 1-hydroxybenzotriazole and, where appropriate, a reaction-inert amine such as N-methylmorpholine or N-ethyldiisopropylamine (for example when either (VI) or the carbodiimide is in the form of an acid addition salt) and/or a catalyst such as 4-dimethylaminopyridine, in a suitable solvent such as dichloromethane. Thus, in one process, (V) is converted to the corresponding acyl chloride using oxalyl chloride and a catalytic amount of dimethylformamide in a suitable solvent, e.g. dichloromethane, at about 0°–5° C. and then the acyl chloride is reacted with (VI), conveniently as its hydrochloride salt, in the presence of N-ethyldiisopropylamine as reaction-inert base in dichloromethane at from about 0° C. to about room temperature.

A compound of formula (IV) may be prepared by N-deprotection of a compound of formula (VII):

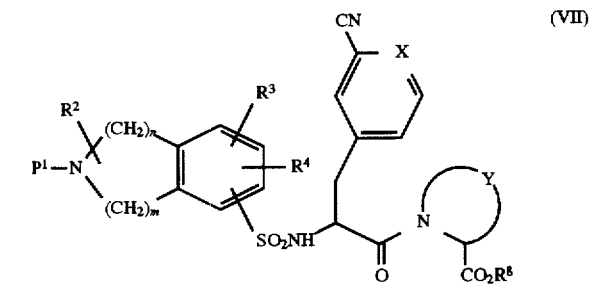

wherein $P^1$ is a protecting group and X, Y, $R^2$, $R^3$, $R^4$, $R^8$, m and n are as previously defined for formula (IV). $p^1$, which represents a conventional amine protecting group, is chosen with due regard to its compatibility with the various reagents employed in earlier synthetic steps of the over-all process and also to the reaction conditions required for its selective removal; preferably, it is trifluoroacetyl. The particular protecting group can be removed under standard conditions which, in the case of trifluoroacetyl, are mild aqueous base optionally in the presence of a $C_1$-$C_3$ alkanol as cosolvent. Preferred conditions are sodium or potassium carbonate in aqueous methanol or ethanol at about room temperature.

A compound of formula (VII) may be prepared by coupling a compound of formula (VIII):

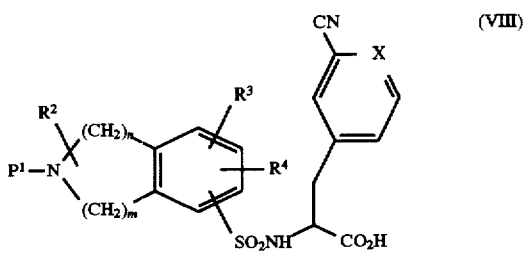

wherein X, $R^2$, $R^3$, $R^4$, m, n and $P^1$ are as previously defined for formula (VII), with a compound of formula (VI), by analogy with the preparation of a compound of formula (III) from a compound of formula (V) as described earlier.

A compound of formula (V) may be prepared by hydrolysis of a compound of formula (IX):

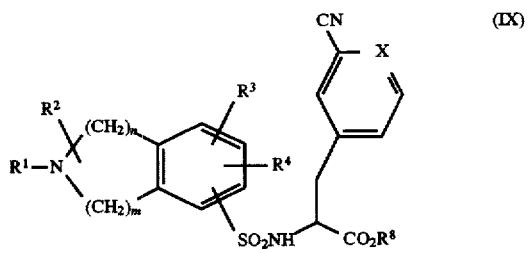

wherein X, $R^1$, $R^2$, $R^3$, $R^4$, m and n are as previously defined for formula (V) and $R^8$ is as previously defined for formula (VI), under conditions described previously for the conversion of (II) to (I).

A compound of formula (IX) may be prepared by N-alkylation of a compound of formula (X):

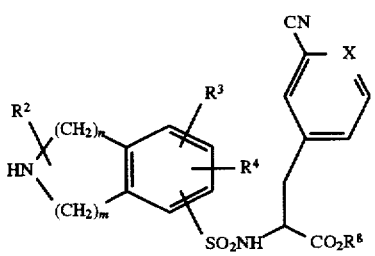 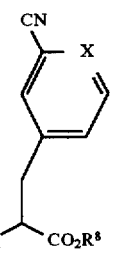 (X)

wherein X, R², R³, R⁴, R⁸, m and n are as previously defined for formula (IX), by analogy with the conversion of (IV) to (III), whilst a compound of formula (X) may, in turn, be prepared from a compound of formula (XI):

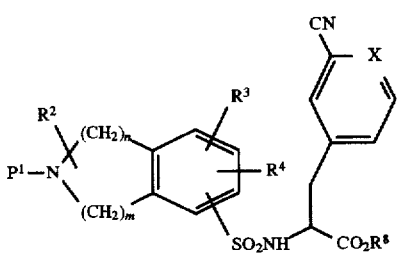 (XI)

wherein X, R², R³, R⁴, R⁸, m and n are as previously defined for formula (X) and P¹ is as previously defined for formula (VIII), under the conditions described for the conversion of (VII) to (IV).

A compound of formula (VIII) may be prepared by sulphonylation of a compound of formula (XII):

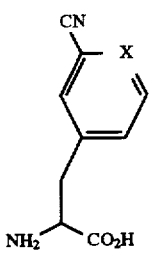 (XII)

wherein X is as previously defined for formula (VIII), with a compound of formula (XIII):

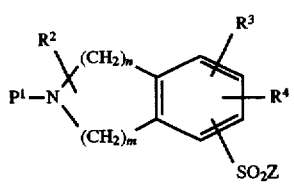 (XIII)

wherein Z is halo, preferably chloro, and R², R³, R⁴, m, n and p¹ are as previously defined for formula (VIII).

The α-amino acid of formula (XII) is firstly doubly protected in situ using a silylating reagent in the presence of a reaction-inert base in a suitable solvent, at from about room temperature to about the reflux temperature of the reaction medium, to afford the N-silyl-O-silyl ester which is then reacted with (XIII) at about the reflux temperature of the reaction medium. A convenient silylating reagent is trimethylsilyl chloride, which is preferably used with N-ethyldiisopropylamine as base in dichloromethane as solvent.

A compound of formula (XI) may also be prepared from (XIII), by conventional sulphonylation of a compound of formula (XIV):

(XIV)

wherein X is as previously defined for formula (XI), in the presence of a reaction-inert base in a suitable solvent at from about 0° C. to about room temperature. In this reaction the α-amino ester is generally used as an acid addition salt, e.g. the hydrochloride, the preferred base is N-methylmorpholine and the solvent preferably dichloromethane.

A compound of formula (XIV) may be prepared by a variety of procedures from the plethora of α-amino acid/ester syntheses available. A convenient method is that involving C-"benzylation" of an appropriately protected glycine derivative, followed by N-deprotection of the resulting phenylalanine derivative. For example, when X is CH and R⁸ is ethyl, N-(diphenylmethylene)glycine ethyl ester is treated with 3-cyanobenzyl bromide in the presence of both a quaternary ammonium salt such as tetrabutylammonium bromide and a base such as potassium carbonate in a suitable solvent, e.g. acetonitrile, at about the reflux temperature of the reaction medium. The crude 3-cyanophenylalanine derivative thus obtained may then be N-deprotected under acidic conditions, e.g. by using aqueous citric acid solution with a suitable cosolvent such as industrial methylated spirit at about room temperature, to afford the required α-amino ester.

Clearly, a compound of formula (XII) is obtainable by standard hydrolysis of a compound of formula (XIV).

In order to prepare the preferred stereoisomers of formula (IA), the (S)-enantiomers of both (XII) and (XIV) are required. Again, a variety of methods is available to the skilled person, ranging from asymmetric synthesis to classical resolution procedures involving appropriate derivatives of (XII) and (XIV). A particularly convenient procedure is enzymic resolution. Thus treatment of (XIV), wherein X is CH and R⁸ is ethyl for example, with α-chymotrypsin in a suitable solvent medium such as aqueous toluene at from about room temperature to about 40° C. provides the (S)-enantiomer of (XII), wherein X is CH, directly.

Conversion of the (S)-enantiomer of (XII) to the (S)-enantiomer of (XIV) can be effected by employing a typical α-amino acid N-protection/deprotection strategy. For example, a conventional amine protecting group such as t-butoxycarbonyl(Boc) or benzyloxycarbonyl(Cbz) is introduced into the former and this intermediate is then converted to a suitably reactive alkali metal salt, preferably the cesium salt, which in turn is alkylated with a compound of formula R⁸Q, wherein Q is as previously defined but is preferably bromo or iodo. Finally, the N-protecting group is removed under standard conditions, e.g. using trifluoroacetic acid or catalytic hydrogenation respectively, and the resulting α-amino ester optionally converted to its hydrochloride salt.

An alternative approach to the (S)-enantiomer of (XII), and hence to that of (XIV), relies upon the accessibility of alanine derivatives which are sufficiently reactive to undergo a transition metal mediated cross-coupling reaction with the appropriate iodo or bromo cyanopyridine/benzonitrile. The recent disclosure (J.Org.Chem.,1992,57,3397) of the organozinc reagent (XV):

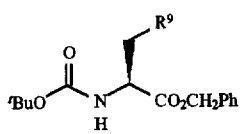

wherein $R^9$ is ZnI, which is prepared from the corresponding 3-iodoalanine derivative (XV; wherein $R^9$ is I) allows such an approach to be realised. Thus, for example, treatment of the former, generated in situ in a suitable solvent such as anhydrous tetrahydrofuran, with 4-bromo-2-cyanopyridine in the presence of a catalytically effective transition metal derivative, e.g. bis(triphenylphosphine)palladium(II) chloride, furnishes the required cyanopyridylalanine derivative of formula (XV) wherein $R^9$ is 2-cyano-4-pyridyl. Conventional base-catalysed ester hydrolysis, followed by removal of the N-Boc protecting group under standard conditions, e.g. using trifluoroacetic acid or hydrogen chloride, provides a compound of formula (XII) wherein X is N.

A compound of formula (XIII) may be prepared from a compound of formula (XVI):

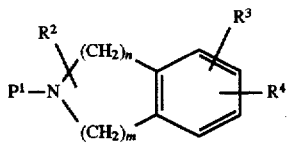

wherein $R^2$, $R^3$, $R^4$, m, n and $p^1$ are as previously defined for formula (XIII), by the application of known methods for the electrophilic introduction of a $SO_2Z$ group, wherein Z is as previously defined for formula (XIII), into an aromatic ring system. For example, when Z is chloro, by the action of chlorosulphonic acid at from about $-10°$ to about $+5°$ C.

A compound of formula (XVI) may be prepared from a compound of formula (XVII):

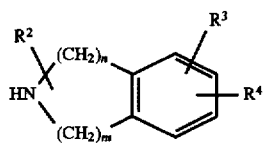

wherein $R^2$, $R^3$, $R^4$, m and n are as previously defined for formula (XVI), by conventional procedures. For example, when $P^1$ is trifluoroacetyl, by using trifluoroacetic anhydride, optionally in the presence of a base such as N-methylmorpholine or N-ethyldiisopropylamine and a solvent such as dichloromethane at from about $0°$ C. to about room temperature.

A compound of formula (VI) may be prepared by a variety of methods, e.g. by standard cyclic α-amino acid/ester syntheses, and, when a particular stereoisomer is required, by classical resolution procedures or by asymmetric synthesis.

For example, when (VI) represents a compound of formula (VIA):

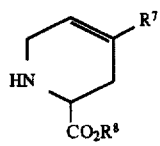

wherein $R^7$ is as previously defined for formula (IB) and $R^8$ is as previously defined for formula (VI), either 4-methylpyridine or 4-ethylpyridine offers a convenient starting point and may be processed as follows. Following guaternisation by alkylation, e.g. using a conventional methylation procedure, the resulting pyridinium salt is subjected to partial reduction using sodium borohydride followed by in situ α-cyanation of the 2,5-dihydropyridine derivative using hydrogen cyanide to afford, in this example, 1-methyl-2(R, S) -cyano-4-methyl/ethyl-1,2,3,6-tetrahydropyridine. Next, the nitrile is converted to the required ester derivative and N-demethylation effected using a suitable chloroformate, e.g. 2,2,2-trichloroethyl chloroformate. Finally, N-deprotection is carried out using the appropriate reagent, e.g. zinc dust in this example.

An alternative approach to a compound of formula (VIA) involves aza Diels-Alder cycloaddition chemistry in which an imine of formula (XVIII), wherein $p^2$ is a suitable protecting group, e.g. benzyl, is reacted with a diene of formula (XIX):

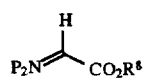

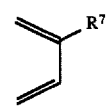

(see Tetrahedron:Asymmetry,1991, 2,1263), followed by N-debenzylation, again using a chloroformate reagent, e.g. 1-chloroethyl chloroformate in this case. The final N-deprotection may be achieved using excess alcohol ($R^8OH$) at about reflux temperature.

Clearly, reduction of (VIA), e.g. by catalytic hydrogenation, will provide the corresponding piperidine-2-carboxylic esters.

When $P^2$ also acts as a chiral auxiliary, e.g. it is 1(R)- or 1(S)-phenylethyl, a useful degree of asymmetric induction is achievable in the (4+2) cycloaddition reaction affording a mixture of easily separable diastereoisomers; the 1(S)-auxiliary induces (R)-stereochemistry at the 2-position and the 1(R)-auxiliary provides the antipodal series (see Tetrahedron:Asymmetry,1991,2,1263). N-Deprotection may be effected as above for the case wherein $P^2$ is benzyl, thus providing either the preferred 2(R)- or the 2(S)-enantiomer of (VIA) respectively.

Again, catalytic hydrogenation of these enantiomers should lead to the (2R,4S)- and (2S,4R)-piperidine enantiomers respectively.

Alternative approaches to these piperidine enantiomers wherein $R^7$ is methyl, and also to the corresponding (2R, 4R)- and (2S,4S)-enantiomers, are described in Biochem.Biophys.Res.Comm.,1981,101,440, in which classical fractional distillation, fractional crystallisation of salts formed from optically active acids (L- and D-tartaric acid) and epimerisation techniques are employed.

Resolution may also be achieved by chromatographic separation procedures. For example, acid-catalysed hydrolysis of the cycloadduct formed from (XVIII) wherein $P^2$ is benzyl, and (XIX), affords 1-benzyl-4-methyl/ethyl-1,2,3,6-tetrahydropyridine-2(R,S)-carboxylic acid which is then esterified under standard conditions with a chiral alcohol, e.g. a N-protected ephedrine derivative such as N-acetyl-(1R,2S)-ephedrine. N-Deprotection using, for example, 2,2,2-trichloroethyl chloroformate followed by zinc dust as described above, followed by chromatography on silica gel, furnishes the individual 2(R)- and 2(S)-diastereoisomeric esters, each of which is processed as follows. N-Reprotection, e.g. using a Boc group, removal of the chiral auxiliary by base-catalysed hydrolysis, reesterification with REOH, and removal of the Boc group, provides the 2(R)- and 2(S)-enantiomers of (VIA) whose identities can be confirmed by comparison with the enantiomers obtained by the asymmetric aza Diels-Alder chemistry previously described.

The bicyclic amines of formula (XVII) and intermediates employed in the preparation thereof, also the iodo or bromo cyanopyridine/benzonitrile required for the preparation of a compound of formula (XV) wherein $R^9$ is 2-cyano-4-pyridyl or 3-cyanophenyl, when neither commercially available nor subsequently described, can be obtained either by analogy with the processes described in the Preparations section or by conventional synthetic procedures, in accordance with standard textbooks on organic chemistry or literature precedent, from readily accessible starting materials using appropriate reagents and reaction conditions.

Moreover, persons skilled in the art will be aware of variations of, and alternatives to, those processes described hereinafter in the Examples and Preparations sections which allow the compounds defined by formula (I) to be obtained.

The pharmaceutically acceptable acid addition salts of the compounds of formula (I) may also be prepared in a conventional manner. For example a solution of the free base is treated with the appropriate acid, either neat or in a suitable solvent, and the resulting salt isolated either by filtration or by evaporation under vacuum of the reaction solvent. Pharmaceutically acceptable base addition salts can be obtained in an analogous manner by treating a solution of a compound of formula (I) with the appropriate base. Both types of salt may be formed or interconverted using ion-exchange resin techniques.

The biological activities of the compounds of the present invention were determined by the following test methods.

Chromogenic Assays

The inhibition of thrombin, trypsin, plasmin or factor Xa is measured in 96 well plate chromogenic assays. The percentage inhibition and $IC_{50}$ are calculated from triplicate samples of an 8 concentration dose-response curve. From the substrate Km and $IC_{50}$, the Ki for each inhibitor is calculated. All assays are carried out in a total incubation of 200 μl of 50 mM HEPES and 150 mM NaCl at pH 8.0, and all compound dilutions are preincubated with enzyme at room temperature for 15 minutes prior to addition of substrate. After 30 minutes incubation at 30° C., the O.D. is measured at 405 nM in a 96 well plate reader. Thrombin activity is measured using bovine thrombin and S2238 (E-D-Phe-Pip-Arg-pNA), bovine pancreatic trypsin is assayed with S2222 (Benz-Isoleu-Glu-Gly-Arg-pNA), bovine plasma plasmin is assayed with Chromozym PL (Tosyl-Gly-Pro-Lys-pNA) and bovine factor Xa is assayed in 50 mM Tris, 150 mM NaCl,pH 7.5 buffer with S2222.

Clotting Assays

Thrombin time (TT) and activated partial thromboplastin time (APTT) are measured using Instrumentation Laboratories (IL) Test TT reagent and IL Test APTT (ellagic acid) reagent respectively in an Automated Coagulation Laboratory (ACL), according to the manufacturer's instructions.

In Vitro

To 1 ml aliquots of rat pooled plasma (citrated), a $\frac{1}{100}$ volume of a range of compound concentrations is added and preincubated at room temperature for 15 minutes, after which the TT and APTT are measured.

Ex Vivo

Compounds are dosed per os, intravenously or intraduodenally to rats. Pre- and post-dose blood samples are taken into citrate solution and plasma prepared. TT and APTT are measured as for in vitro assays.

In therapy, the compounds of formula (I), their pharmaceutically acceptable salts, and pharmaceutically acceptable solvates of either entity, can be administered alone, but will generally be administered in admixture with a pharmaceutical carrier selected with regard to the intended route of administration and standard pharmaceutical practice. Preferably, they are administered orally in the form of tablets containing such excipients as starch or lactose, or in capsules or ovules either alone or in admixture with excipients, or in the form of elixirs, solutions or suspensions containing flavouring or colouring agents. They can also be injected parenterally, for example intravenously, intramuscularly or subcutaneously. For parenteral administration, they are best used in the form of a sterile aqueous solution which may contain other substances, for example enough salts or glucose to make the solution isotonic with blood. For buccal or sublingual administration they may be administered in the form of tablets or lozenges which can be formulated in a conventional manner.

For oral, parenteral, buccal and sublingual administration to patients, the daily dosage level of the compounds of formula (I) and their pharmaceutically acceptable salts and solvates will be from 1 to 1000 mg (in single or divided doses). Thus tablets or capsules may contain from 0.5 to 500 mg of active compound for administration singly, or two or more at a time, as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited and such are within the scope of this invention.

Thus the invention provides a pharmaceutical composition comprising a compound of formula (I), or a pharmaceutically acceptable salt thereof, or a pharmaceutically acceptable solvate of either entity, together with a pharmaceutically acceptable diluent or carrier.

The invention also provides a compound of formula (I), or a pharmaceutically acceptable salt thereof, or a pharmaceutically acceptable solvate of either entity, or a pharmaceutical composition containing any of the foregoing, for use as a medicament.

The invention further includes the use of a compound of formula (I), or a pharmaceutically acceptable salt thereof, or a pharmaceutically acceptable solvate of either entity, or a pharmaceutical composition containing any of the foregoing, for the manufacture of a medicament for the curative or prophylactic treatment of deep vein thrombosis (DVT) after surgery, major medical illness, paralysis, malignancy, prolonged immobilisation trauma, application of lower limb plaster casts, or fractures of the lower limbs or pelvis; recurrent DVT; DVT during pregnancy when there is a previous history thereof; reocclusion following thrombolytic therapy; chronic arterial obstruction; peripheral vascular disease ; acute myocardial infarction; unstable angina; atrial fibrillation; thrombotic stroke; transient ischaemic attacks; disseminated intravascular coagulation; coagulation in extra-corporeal circuits; occlusion of arterio-venous shunts and blood vessel grafts (including coronary artery by-pass grafts); restenosis and occlusion following angioplasty; neurodegenerative disorders; inflammatory disorders; or scarring.

In a further aspect, the invention provides a method of treating a mammal (including a human being) to cure or prevent deep vein thrombosis (DVT) after surgery, major medical illness, paralysis, malignancy, prolonged immobilisation trauma, application of lower limb plaster casts, or fractures of the lower limbs or pelvis; recurrent DVT; DVT during pregnancy when there is a previous history thereof; reocclusion following thrombolytic therapy; chronic arterial obstruction; peripheral vascular disease; acute myocardial infarction; unstable angina; atrial fibrillation; thrombotic stroke; transient ischaemic attacks; disseminated intravascular coagulation; coagulation in extra-corporeal circuits; occlusion of arterio-venous shunts and blood vessel grafts (including coronary artery by-pass-grafts); restenosis and occlusion following angioplasty; neurodegenerative disorders; inflammatory disorders; or scarring; which comprises treating said mammal with an effective amount of a compound of formula (I), or a pharmaceutically acceptable salt thereof, or a pharmaceutically acceptable solvate of either entity, or a pharmaceutical composition containing any of the foregoing.

The syntheses of the compounds of the invention and of the intermediates for use therein are illustrated by the following Examples and Preparations. The purity of the compounds was routinely monitored by thin layer chromatography (Rf) using Merck Kieselgel 60 $F_{254}$ plates and the following solvent systems (SS):

1. hexane:ether, 1:1;
2. ether;
3. dichloromethane:methanol:glacial acetic acid, 90:10:1;
4. hexane:ether,4:1;
5. dichloromethane;
6. dichloromethane:methanol:0.880 aqueous ammonia, 95:5:0.5;
7. hexane:ethyl acetate,3:7;
8. hexane:ethyl acetate,1:1;
9. dichloromethane:methanol:0.880 aqueous ammonia, 90:10:1;
10. hexane:ethyl acetate,3:1;
11. toluene:ethyl acetate,4:1;
12. toluene:ethyl acetate,1:1;
13. isobutyl methyl ketone:glacial acetic acid:water,2:1:1 (upper phase);
14. ethyl acetate:ethanol,4:1;
15. ethyl acetate:ethanol:glacial acetic acid,90:10:0.4;
16. ethyl acetate:ethanol:glacial acetic acid,80:20:1;
17. ethyl acetate:ethanol,9:1;
18. hexane:ethyl acetate:diethylamine,9:1:0.2;
19. hexane:ethyl acetate,50:1;
20. dichloromethane:methanol,97.5:2.5;
21. dichloromethane:ethanol,97.5:2.5;
22. hexane:ethyl acetate,1:4;
23. dichloromethane:methanol,95:5;
24. dichloromethane:methanol:0.880 aqueous ammonia, 80:20:5;
25. dichloromethane:methanol:0.880 aqueous ammonia, 84:14:2.

$^1$H Nuclear magnetic resonance (NMR) spectra were recorded using either a Nicolet QE-300 or a Bruker AC-300 spectrometer and were in all cases consistent with proposed structures.

Mass spectra were obtained with a Fisons Instrument Trio 1000 spectrometer using thermospray ionisation.

Room temperature means 20°–25° C.

EXAMPLE 1

4-Methyl-1-[N-(2-methyl-1,2,3,4-tetrahydroisocauinoline-7-sulphonyl)-3-amidino-(S)-phenylalanyl]-1,2,3,6-tetrahydropyridine-2(R)-carboxylic acid 1M Aqueous sodium hydroxide solution (16.4 ml, 16.4 mmol) was added to a stirred solution of 4-methyl-1-[N-(2-methyl-1,2,3,4-tetrahydroisoquinoline-7-sulphonyl)-3-amidino-(S)-phenylalanyl]-1,2,3,6-tetrahydropyridine-2(R)-carboxylic acid ethyl ester hydrochloride (Preparation 67; 1.99 g, 3.29 mmol) in 1,4-dioxan (15 ml). After 3.5 hours at room temperature, the excess sodium hydroxide was carefully neutralised by the dropwise addition of 1M hydrochloric acid and the resulting clear solution evaporated to dryness under reduced pressure. The residue was extracted with a hot mixture of dichloromethane and 2-propanol (1:1), then the extract filtered and the filtrate evaporated under reduced pressure to afford the title compound (1.80 g) as a white solid. Rf 0.12 (SS 13). $[\alpha]_D^{25}+44°$ (c=0.1, $CH_3OH$). Found: C,55.75; H,6.34; N,11.01. $C_{27}H_{33}N_5O_5S$; 2.50 $H_2O$; 0.50 $(CH_3)_2CHOH$ requires C,55.62; H,6.49; N,10.99%.

This compound may be further purified as its dihydrochloride salt by reversed phase chromatography on MCI Gel CHP-20P (styrene-divinylbenzene polymer; Mitsubishi Kasei Corp.), using water:methanol (4:1) as eluent, to provide a white foam, which may be ground to a white powder. Rf 0.12 (SS 13) and 0.30 (SS 24). $[\alpha]_D^{25}+61.8°$ (c=0.1, $CH_3OH$). Found: C,50.34; H. 6.15; N, 10.73. $C_{27}H_{33}N_5O_5S$; 2HCl; 2$H_2O$ requires C,50.00; H. 6.06; N,10.79%.

The title compounds of Examples 2–15 were obtained by hydrolysis of the corresponding ethyl ester precursor (Preparation 68–81 respectively) using the procedure described in Example 1. In cases wherein excess hydrochloric acid was used in the work-up, the title compounds were isolated as hydrochloride salts after extraction with hot 2-propanol followed by, where necessary, trituration with ether or ethyl acetate.

EXAMPLE 2

4-Methyl-1-[N-(2-methyl-1,2,3,4-tetrahydroisoquinoline-6-sulphonyl)-3-amidino-(S)-phenylalanyl]-1,2,3,6-tetrahydropyridine-2(R)-carboxylic acid dihydrochloride Obtained from Preparation 68 as a white solid. Rf 0.11 (SS 24). Found: C,51.71; H,6.11; N,10.49. $C_{27}H_{33}N_5O_5S$; 2HCl; $H_2O$; 0.25 $(CH_3 CH_2)_2O$ requires C,51.80; H,6.13; N,10.79%.

EXAMPLE 3

4-Methyl-1-[N-(3-methyl-2,3,4,5-tetrahydro-1H-3-benzazepine-7-sulphonyl)-3-amidino-(S)-phenylalanyl]-1,2,3,6-tetrahydropyridine-2(R)-carboxylic acid dihydrochloride Obtained from Preparation 69 as a white solid. Rf 0.14 (SS 13). Found: C,51.95; H,6.46; N,10.03. $C_{28}H_{35}N_5O_5S$; 2HCl; $H_2O$; 0.30 $(CH_3)_2CHOH$ requires C,52.38; H,6.30; N,10.57%.

EXAMPLE 4

1-[N-(1(R, S)-Methoxymethyl-2-methyl-1,2,3,4-tetrahydroisoquinoline-7-sulphonyl)-3-amidino-(S)-phenylalanyl]-4-methyl-1,2,3,6-tetrahydropyridine-2(R)-carboxylic acid dihydrochloride Obtained from Preparation 70 as a white powder. Rf 0.13 (SS 13). Found: C,51.86; H,6.45; N,9.76. $C_{29}H_{37}N_5O_6S$; 2HCl; $H_2O$; 0.20 $(CH_3CH_2)_2O$ requires C,51.75; H,6.30; N,10.19%.

EXAMPLE 5

1-{N-[1(R,S)-(N,N-Dimethylcarbamoylmethyl)-2-methyl-1,2,3,4-tetrahydroisoquinoline-7-sulphonyl]-3-amidino- (S)-phenylalanyl}-4-methyl-1,2,3,6-tetrahydropyridine-2 (R)-carboxylic acid dihydrochloride Obtained from Preparation 71 as a white amorphous powder. Rf 0.25 (SS 24) and 0.12 (SS 13). Found:C,51.62; H,6.54; N,10.96. $C_{31}H_{40}N_6O_6S$; 2HCl; 1.50 $H_2O$; 0.31 $(CH_3)_2CHOH$ requires C,51.58; 1,6.43; N,11.31%

EXAMPLE 6

4-Methyl-1-[N-(2,5-dimethyl-1,2,3,4-tetrahydroisoquinoline-8-sulphonyl)-3-amidino-(S)-phenylalanyl]-1,2,3,6-tetrahydropyridine-2(R)-carboxylic acid dihydrochloride Obtained from Preparation 72 as a white foam. Rf 0.61 (SS 24). m/e 554 $(M+H)^+$.

EXAMPLE 7

4-Ethyl-1-[N-(2-methyl-1,2,3,4-tetrahydroisoquinoline-7-sulphonyl)-3-amidino-(S)-phenylalanyl]-1,2,3,6-tetrahydropyridine-2(R,S)-carboxylic acid dihydrochloride Obtained from Preparation 73 as a colourless solid. Rf 0.18 (SS 25). Found: C,51.13; H,6.45; N,10.06. $C_{28}H_{35}N_5O_5S$; 2HCl; 1.90 $H_2O$ requires C,50.72; H,6.20; N,.10.57%.

EXAMPLE 8

4-Methyl-1-{N-[3-(2-propyl-2,3,4,5-tetrahydro-1H-3-benzazenine-7-sulphonyl]-3-amidino-(S)-phenvyalanyl}-1,2,3,6-tetrahydropyridine-2(R)-carboxylic acid dihydrochloride Obtained from Preparation 74 as a white solid. Rf 0.21 (SS 24). Found: C,54.33; E,7.19; N,9.19. $C_{30}H_{39}N_5O_5S$; 2HCl; $H_2O$; $(CH_3)_2CHOH$ requires C,54.09; H,7.02; N,9.56%.

EXAMPLE 9

1-{N- [3-(3-Dimethylamino-1-propyl)-2,3,4,5-tetrahydro-1H-3-benzazenine-7-sulphonyl]-3-amidino-(S)-phenylalanyl}-4-methyl-1,2,3,6-tetrahydropyridine-2(R)-carboxylic acid dihydrochloride Obtained from Preparation 75 as a cream powder. Rf 0.16 (SS 24). m/e 625 $(M+H)^+$.

EXAMPLE 10

1-[N-(2-Benzyl-1,2,3,4-tetrahydroisoquinoline-7-sulphonyl)-3-amidino-(S)-phenylalanyl]-4-methyl-1,2,3,6-tetrahydropyridine-2(R)-carboxylic acid dihydrochloride Obtained from Preparation 76 as a white solid. Rf 0.38 (SS 13). Found: C,54.36; H,6.00; N,9.39. $C_{33}H_{37}N_5O_5S$; 2HCl; 2$H_2O$; 0.30 $(CH_3)_2CHOH$ requires C,54.87; H,6.18; N,9.41%.

EXAMPLE 11

4-Methyl-1-[N-(2-methyl-1,2,3,4-tetrahydroisoquinoline-7-sulphonyl)-3-amidino-(S)-phenylalanyl]-1,2,3,6-tetrahydropyridine-2(S)-carboxylic acid hydrochloride Obtained from Preparation 77 as a white solid. Rf 0.24 (SS 24). Found: C,54.43; H,6.21; N,11.36.$C_{27}H_{33}N_5O_5S$; HCl; $H_2O$; 0.27 $(CH_3)_2CHOH$ requires C,54.72; H,6.31; N,11.48%.

EXAMPLE 12

4-Methyl-1-{N-[2-(2-propyl)-1,2,3,4-tetrahydroisoquinoline-7-sulphonyl]-3-amidino-(S)-phenylalanyl}-1,2,3,6-tetrahydropyridine-2(R)-carboxylic acid Obtained from Preparation 78 as a white solid. Rf 0.35 (SS 24). Found: C,59.59; H,6.56; N,11.46. $C_{29}H_{37}N_5O_5S$; $H_2O$; 0.33 $CH_3CO_2CH_2CH_3$ requires C,59.22; H,6.83; N,11.39%.

EXAMPLE 13

4(R)-Methyl-1-[N-(2-methyl-1,2,3,4-tetrahydroisoquinoline-7-sulphonyl)-3-amidino-(R,S)-phenylalanyl]piperidine-2(R)-carboxylic acid dihydrochloride Obtained from Preparation 79 as a white amorphous solid. Rf 0.05 (SS 13). Found: C,50.85; H,6.01; N,10.78. $C_{27}H_{35}N_5O_5S$; 2HCl; 1.50 $H_2O$ requires C,50.54; H,6.28; N,10.91%.

EXAMPLE 14

4-Methyl-1-[N-(2-methyl-1,2,3,4-tetrahydroisoquinoline-7-sulphonyl)-3-(2-amidino-4-pyridyl)-(S)-alanyl]-1,2,3,6-tetrahydropyridine-2(R)-carboxylic acid dihydrochloride Obtained from Preparation 80 as a foam. Rf 0.12 (SS 13). Found: C,48.98; E,5.95; N,12.23. $C_{26}H_{32}N_6O_5S$; 2HCl; $H_2O$; 0.17 $(CH_3)_2CHOH$ requires C,49.60; E,5.86; N,13.09%.

EXAMPLE 15

4-Methyl-1-[N-(1,2,3,4-tetrahydroisoquinoline-7-sulphonyl)-3-amidino-(S)-phenylalanyl]-1,2,3,6-tetrahydropyridine-2(R,S)-carboxylic acid dihydrochloride Obtained from Preparation 81 as a white solid. Rf 0.13 (SS 13). Found: C,51.72; H,5.78; N,10.69. $C_{26}H_{31}N_5O_5S$; 2HCl requires C,51.60; H,5.83; N,11.24%.

PREPARATION 1

2-Trifluoroacetyl-1,2,3,4-tetrahydroisoquinoline-7-sulphonyl chloride (a) 2-Trifluoroacetyl-1, 23 4-tetrahydroisoquinoline This intermediate was obtained by the method described in J. Med. Chem., 1980, 23, 837 and used directly in step (b).

The title compound was also obtained by the method described in J. Med. Chem., 1980, 23, 837, using the intermediate from (a) above, as a white solid (52.9% yield based on 1,2,3,4-tetrahydroisoquinoline), m.p. 104°–105° C., after crystallisation from ether. Rf 0.25 (SS 1).

PREPARATION 2

2-Trifluoroacetyl-1,2,3,4-tetrahydroisoquinoline-6-sulphonyl chloride

Crystallisation of material recovered from the mother-liquors of Preparation l(b), from diisopropyl ether, afforded the title compound (3.6% yield based on 1,2,3,4-tetrahydroisoquinoline), m.p. 110°–112° C. Rf 0.36 (SS 1).

PREPARATION 3

3-Trifluoroacetyl-2,3,4,5-tetrahydro-1H-3-benzazenine-7-sulphonyl chloride (a) 2,3,4,5-Tetrahydro-1H-3-benzazenine This starting material was obtained by the method described in Helv. Chim. Acta, 1935, 18, 1388.

(b) 3-Trifluoroacetyl-2,3,4,5-tetrahydro-1H-3-benzazepine

Trifluoroacetic anhydride (6.0 g, 28.56 mol) was added dropwise over 20 minutes to a stirred, ice-cooled solution of the material from (a) above (4.2 g, 28.56 mmol) and N-methylmorpholine (2.89 g, 28.56 mmol) in dichloromethane (45 ml). After 2.5 hours at room temperature, the reaction solution was washed successively with water, 1M aqueous citric acid solution and water, dried (MgSO$_4$) and evaporated under reduced pressure to yield a yellow solid, which was triturated with hot hexane. Filtration, concentration and cooling of the combined hexane solutions afforded the required product (5.96 g) as a pale yellow solid, m.p. 78°–80° C. Found: C,58.85; H,4.93; N,5.75. C$_{12}$H$_{12}$F$_3$NO requires C,59.25; H,4.97; N,5.76%.

(c)

Chlorosulphonic acid (10.4 ml, 0.156 mol) was added dropwise to a stirred, cold solution of the product from (b) above (5.85 g, 11.7 mmol) in dichloromethane, whilst ensuring that the temperature of the reaction mixture was held between −12° and −8° C. After 2 days at room temperature, the reaction solution was poured onto ice and the aqueous phase separated and extracted with dichloromethane. The combined organic extracts were dried (MgSO$_4$) and evaporated under reduced pressure to provide an oil (7.9 g) which was purified by chromatography on silica gel, using a mixture of hexane and ether (1:3) as eluent, to give the title compound as a colourless oil which eventually solidified. Crystallisation of a sample from diisopropyl ether produced a white solid, m.p. 87°–88° C. Found: C,41.75; E,3.18; N,3.92. C$_{12}$H$_{11}$F$_3$ClNO$_3$S requires C,42.17; H,3.24; N,4.10%.

PREPARATION 4

1(R,S)-Methoxymethyl-2-trifluoroacetyl-1,2,3,4-tetrahydroisoquinoline-7-sulphonyl chloride (a) N-Methoxyacetyl-2-phenylethylamine Methoxyacetyl chloride (19.57 g, 0.18 mol) was added over 10 minutes to a stirred, ice-cooled solution of 2-phenylethylamine (21.85 g, 0.18 mol) and N-ethyldiisopropylamine (23.26 g, 0.18 mol) in dichloromethane (200 ml). After 2 hours at room temperature, the solvent was removed under reduced pressure and the residue partitioned between ether and water. The organic phase was washed successively with 1M aqueous citric acid solution, water, saturated aqueous sodium bicarbonate solution and water, dried (MgSO$_4$) and evaporated under reduced pressure to provide the required product (29.65 g) as an oil. Rf 0.32 (SS 2), which was used without further purification in the next step.

(b) 1-Methoxymethyl-3,4-dihydroisoquinoline

Phosphorous pentoxide (25 g, 0.176 mol) was added to a stirred solution of the product from (a) above (14.47 g, 0.075 mol) in xylene (35 ml) and the resulting mixture heated under reflux for 2.5 hours. The solvent was decanted from the resulting black gum which was triturated with xylene and then, when cool, with ether. Water was then carefully added, with ice-cooling, and the resulting mixture basified with 2M aqueous sodium hydroxide solution and then extracted with ether. The extract was washed with water, dried (MgSO$_4$) and evaporated under reduced pressure to give a brown oil (13.4 g) which was purified by chromatography on silica gel, using ether as eluent, to afford the required compound (5.88 g) as an orange oil. Rf 0.28 (SS 2).

(c) 1(R,S)-Methoxymethyl-1,2,3,4-tetrahydroisoquinoline

Sodium triacetoxyborohydride (8.11 g, 38.3 mmol) was added to a stirred, ice-cooled solution of the product from (b) above (6.1 g, 34.8 inmol) in methanol (80 ml), then the resulting mixture stirred for 18 hours at room temperature before being quenched with water. The bulk of the solvent was removed under reduced pressure, then the residue basified with 1M aqueous sodium hydroxide solution and extracted with dichloromethane. The extract was washed with saturated brine, dried (MgSO$_4$) and evaporated under reduced pressure to furnish the required product (6.19 g) as an orange oil, Rf 0.25 (SS 3), m/e 178 (M+H)$^+$, which was used without further purification in the next step.

(d) 1(R,S)-Methoxymethyl-2-trifluoroacetyl-1,2,3,4-tetrahydroisoquinoline

Trifluoroacetic anhydride (10.26 ml, 72.6 mmol) was added dropwise over 0.5 hour to a stirred, ice-cooled solution of the product from (c) above (12.26 g, 69.17 mmol) and N-methylmorpholine (7.35 g, 72.6 mmol) in dichloromethane (150 ml). After 2 hours at room temperature, the solvent was removed under reduced pressure and the residue partitioned between ether and water. The organic phase was washed successively with water basified to pH ca. 8 with sodium bicarbonate, 1M aqueous citric acid solution and water, dried (MgSO$_4$) and evaporated under reduced pressure to provide an oil (19.45 g) which was purified by chromatography on silica gel, using a mixture of hexane and ether (4:1) as eluent, to give the required compound (16.16 g) as a clear oil. Rf 0.27 (SS 4). Found: C,56.83; H,5.19; N,5.02. C$_{13}$H$_{14}$F$_3$NO$_2$ requires C,57.14; H,5.16; N,5.12%.

(e)

The title compound was obtained from the product of (d) above, using the method of Preparation 3(c), as a pale yellow oil which solidified when chilled. Rf 0.35 (SS 5).

PREPARATION 5

1(R,S)-(N,N-Dimethylcarbamoylmethyl)-2-trifluoroacetyl-1,2,3,4-tetrahydroisoquinoline-7-sulphonyl chloride (a) 1(R,S)-(N,N-Dimethylcarbamoylmethyl)-2-trifluoroacetyl-1,2,3,4-tetrahydroisoquinoline 1Ethoxycarbonylmethyl-1,2,3,4-tetrahydroisoquinoline (13.15 g, 60 mmol), obtained by the method described in J. Org. Chem., 1965, 30, 3667, was dissolved in a 30% solution of dimethylamine in ethanol (100 ml). Dimethylamine (32 g) was added and the reaction mixture heated in a steel bomb at 120° C. for 24 hours and at 150° C. for a further 24 hours, then evaporated under reduced pressure to provide the required crude amide (12.9 g) as an oil, Rf 0.13 (SS 3) plus trace of ester starting material at Rf 0.33, which was used without further purification in the next step.

Trifluoroacetic anhydride (12.12 g, 72 mmol) was added dropwise over 0.5 hour to a stirred, ice-cooled solution of the crude amide (12.9 g) and N-ethyldiisopropylamine (10.34 g, 80 mmol) in dichloromethane (120 ml). After 3 hours at room temperature, the solvent was removed under reduced pressure and the residue partitioned between ether and water. The organic phase was washed successively with water, 5% aqueous sodium bicarbonate solution, 1M aqueous citric acid solution and water, dried (MgSO$_4$) and evaporated under reduced pressure to give an orange oil which was purified by chromatography on silica gel, using a mixture of hexane and ethyl acetate (3:7) as eluent, to furnish the required compound (14.3 g). Rf 0.35 (SS 7). Found: C,56.88; H,5.38; N,8.85. C$_{15}$H$_{17}$F$_3$N$_2$O$_2$ requires C,57.32; H,5.45; N,8.91%.

(b)

The title compound (84% yield) was obtained from the product of (a) above, using the procedure of Preparation 3(c), as a white foam. Rf 0.47 (SS 7).

PREPARATION 6

5-Methyl-2-trifluoroacetyl-1,2,3,4-tetrahydroisoquinoline-8-sulphonyl chloride (a) 5-Methylisoquinoline A 3M solution of methyl magnesium iodide in ether (50 ml, 0.15 mol) was added dropwise to a stirred, ice-cooled solution of 5-bromoisoquinoline (21 g, 0.10 mol), obtained by the method described in J. Org. Chem., 1904, 29, 329, and [1,3-bis(diphenylphosphino)-propane]nickel(II) chloride (400 mg, 0.7 mmol) in anhydrous ether and the reaction mixture heated under reflux for 5 days, allowed to cool, then poured into water (500 ml). The organic phase was separated, combined with ether extracts of the aqueous phase, washed with saturated brine, dried ($MgSO_4$) and evaporated under reduced pressure to yield an oil, chromatography of which on silica gel, using a 5–50% ether in hexane elution gradient, provided the required product (8.4 g). Rf 0.40 (SS 8), m/e 144 $(M+H)^+$. Found: C,79.57; H,6.26; N,8.61. $C_{10}H_9N$; 0.27 $CH_3CO_2CH_2CH_3$ requires C,79.70; H,6.74; N,8.39%.

However, the major component of the chromatographic purification procedure was a mixture (18.4 g) of product and starting material which, on crystallisation from hexane, afforded a 2:1 mixture (14.8 g) of 5-bromoisoquinoline and 5-methylisoquinoline.

(b)

A stirred, ice-cooled solution of the above 2:1 mixture (14.3 g) in dichloromethane (150 ml) was saturated with hydrogen chloride and then evaporated under reduced pressure to afford the corresponding hydrochloride salt which was collected and dried.

A stirred mixture of platinum oxide (1g) and a solution of the preceding hydrochloride salt in ethanol (150 ml) was hydrogenated for 30 hours at 50 psi (3.45 bar) and room temperature, then filtered. The filtrate was evaporated under reduced pressure and the residue chromatographed on silica gel, using a mixture of dichloromethane:methanol: 0.880 aqueous ammonia solution (90:10:1) as eluent, to give an 85:15 mixture (5.62 g) of 5-methyl-1,2,3,4-tetrahydroisoquinoline and 5-bromo-1,2,3,4-tetrahydroisoquinoline as an oil; major component: Rf 0.32 (SS 9), m/e 148 $(M+H)^+$.

The above 85:15 mixture was converted to the corresponding 2-trifluoroacetyl derivative mixture, using the procedure described in Preparation 3(b), to afford an oil; major component: Rf 0.90 (SS 10), m/e 244 $(M+H)^+$.

The above crude mixture containing 85% of 5-methyl-2-trifluoroacetyl-1,2,3,4-tetrahydroisoquinoline, was chlorosuphonated following the procedure described in Preparation 3(c) to provide a yellow solid which, on purification by chromatography on silica gel using an elution gradient of 10–50% ethyl acetate in hexane, gave the title compound as a white solid, m.p. 152°–153° C. Found: C,42.18; H,3.24; N,4.10. $C_{12}H_{11}F_3ClNO_3S$ requires C,42.12; H,3.10; N,3.85%.

PREPARATION 7

3-Cyano-(R,S)-phenylalanine ethyl ester

A stirred mixture of 3-cyanobenzyl bromide (300 g, 1.531 mol), N-(diphenylmethylene)glycine ethyl ester (450 g, 1.684 mol), tetrabutylammonium bromide (50.0 g, 0.153 mol), anhydrous potassium carbonate (528.2 g, 3.827 m) and acetonitrile (2.3 l) was heated under reflux for 6.5 hours, allowed to cool, then filtered. The residue obtained by evaporation under reduced pressure of the filtrate was dissolved in ether (2 l), then this solution was washed with water (5×1 l), dried ($MgSO_4$) and evaporated under reduced pressure to provide a yellow oil (595.5 g).

A solution of citric acid (358.96 g, 1.708 mol) in water (1.4 l) was added to a stirred solution of the above yellow oil (497.1 g, 1.30 mol) in industrial methylated spirit (2.5 l ). The resulting milky solution was stirred at room temperature for 20 hours, concentrated under reduced pressure to about half-volume, diluted with water (1.5 l) and extracted with ether. The pH of the aqueous phase was adjusted to ca. 9.5 using solid sodium carbonate, then extraction with ethyl acetate (3×800 ml) effected. Evaporation under reduced pressure of the dried ($MgSO_4$), combined extracts gave the title compound (160.0 g) as a yellow oil, Rf 0.50 (SS 6).

PREPARATION 8

3-Cyano-(S)-phenylalanine

α-Chymotrypsin (2.55 g) was added to a stirred mixture of 3-cyano-(R,S)-phenylalanine ethyl ester (Preparation 7; 187.0 g, 0.857 mol), water (100 ml) and toluene (1.0 l). After 3 hours at room temperature, the reaction mixture was stirred at 65° C. for 0.5 hour then allowed to cool and filtered. The resulting white solid was washed with ether, then dried at 65° C. in vacuo to afford the title compound (68.2 g), m.p. 248°–250° C. $[\alpha]_D^{25}$–14.7° (c=1, 1M HCl). Found: C,62.39; H,5.37; N,14.24. $C_{10}H_{10}N_2O_2$;0.10 $H_2O$ requires C,62.55; H,5.35; N,14.59%

PREPARATION 9

3-Cyano-(S)-phenylalanine ethyl ester hydrochloride (a) N-t-Butoxycarbonyl-3-cyano-(S)-phenylalanine Anhydrous sodium carbonate (16.7 g, 158 mmol) was added to a stirred suspension of 3-cyano-(S)-phenylalanine (Preparation 8; 15.0 g, 78.8 mmol) in water (225 ml), followed by the dropwise addition over 0.5 hour of a solution of di-t-butyl dicarbonate (25.8 g, 115 mmol) in tetrahydrofuran (75 ml). After a further 20 hours, the reaction mixture was concentrated by removal of the bulk of the tetrahydrofuran under reduced pressure, filtered and washed with ethyl acetate. The pH of the aqueous solution was adjusted to ca. 3 with citric acid, then extraction with ethyl acetate effected. The combined organic extracts were washed successively with 1M aqueous citric acid solution and saturated brine, dried ($MgSO_4$) and evaporated under reduced pressure to furnish an oil which was induced to crystallise from a hexane-ether mixture to give the required product (18.5 g) as a white solid, m.p. 122°–124° C.

(b)

A mixture of cesium carbonate (10.38 g, 31.9 mmol) and water (65 ml) was added to stirred solution of the product from (a) above (18.5 g, 63.7 mmol) in acetonitrile (65 ml). The resulting clear solution was evaporated to dryness under reduced pressure and the residue dried azeotropically using toluene to provide the crude cesium salt as a white solid which was then dissolved in dimethylformamide (75 ml) and the stirred solution treated with ethyl iodide (10.93 g, 70 mmol). After 20 hours at room temperature, the reaction mixture was diluted with ether and the resulting suspension washed with water. The combined aqueous washings were extracted with ether, then the organic solution and extracts combined, washed further with water, dried ($MgSO_4$) and evaporated under reduced pressure to furnish a clear oil (19.5 g) which eventually solidified.

This intermediate was dissolved in dichloromethane (100 ml) and trifluoroacetic acid (50 ml) added dropwise over 15 minutes to the stirred solution. After 2 hours, the reaction mixture was evaporated under reduced pressure whilst maintaining the temperature below 30° C. Residual trifluoroacetic acid was removed azeotropically using toluene, the resulting oil dissolved in water (200 ml), then this solution basified with solid sodium bicarbonate and extracted with dichloromethane. The extract was washed with saturated aqueous sodium bicarbonate solution, dried ($MgSO_4$), treated with excess ethereal hydrogen chloride and evaporated under reduced pressure to give a foam which, under ether, solidified to afford the title compound (14.25 g) as a white powder, m/e 219 (M+H)$^+$.

PREPARATION 10

4-Bromo-2-cyanopyridine

The title compound was prepared from 4-bromopyridine-1-oxide (Rec. Trav. chim., 1951, 70, 581) and trimethylsilyl cyanide, using the procedure described in Chem. Pharm. Bull., 1985, 33, 565, and obtained as a solid (49% yield), m.p. 88°–93° C. Rf 0.53 (SS 11). Found: C,39.15; H,1.50; N,15.07. C$_6$H$_3$BrN$_2$ requires C,39.37; E,1.65; N,15.30%.

PREPARATION 11

N-t-Butoxycarbonyl-3-(2-cyano-4-pyridyl)-(S)-alanine benzyl ester 1,2-Dibromoethane (13 μl, 0.14 mmol) was added, under dry nitrogen, to a stirred suspension of zinc dust (240 mg, 3.6 mmol) in anhydrous tetrahydrofuran (1 ml), then the resulting mixture gently heated until the first sign of boiling was evident and allowed to cool to room temperature; this process was repeated twice, after which trimethylsilyl chloride (15 μl, 0.11 mmol) was added and stirring continued for 15 minutes at room temperature. A solution of benzyl 2(R)-t-butoxycarbonylamino-3-iodopropionate (0.5 g, 1.2 mmol), obtained by the method described in J. Org. Chem., 1992, 57, 3397, in anhydrous tetrahydrofuran (2 ml) was next added over 1 minute. After a further 1.5 hours at room temperature, the reaction mixture was treated with bis(triphenylphosphine)palladium(II) chloride (75 mg, 0.1 mmol), followed by 4-bromo-2-cyanopyridine (Preparation 10; 270 mg, 1.4 mmol), and stirred for 18 hours more at room temperature, before being treated with ethyl acetate (10 ml) and saturated aqueous ammonium chloride solution (5 ml) and then filtered. The organic phase was separated, washed successively with 1M aqueous citric acid solution, saturated aqueous sodium bicarbonate solution and saturated brine, dried (MgSO$_4$) and evaporated under reduced pressure. The residue was purified by chromatography on silica gel, using an elution gradient of ethyl acetate:toluene (0:100 to 25:75), to afford the title compound (250 mg) as an oil which subsequently presented as a white foam, m.p. 74°–76° C. Rf 0.59 (SS 12). [α]$_D^{25}$ −24° (c=0.1, CH$_3$OH). Found: C,66.14; H,5.91; N,10.75. C$_{21}$H$_{23}$N$_3$O$_4$ requires C,66.12; H 6.08; N,11.02%.

PREPARATION 12

N-t-Butoxycarbonyl-3-(2-cyano-4-pyridyl)-(S)-alanine

1M Aqueous sodium hydroxide solution (10.8 ml, 10.8 mmol) was added dropwise over 5 minutes to a stirred, ice-cooled solution of N-t-butoxycarbonyl-3-( 2-cyano-4-pyridyl)-(S)-alanine benzyl ester (Preparation 12; 2.73 g, 7.1 mmol) in 1,4-dioxan and the resulting solution allowed to warm to room temperature. After 1.5 hours, the pH of the solution was adjusted to 9 using 2M hydrochloric acid and the bulk of the organic solvent removed under reduced pressure. The residual aqueous solution was washed with ethyl acetate, acidified with solid citric acid and extracted with ethyl acetate, then the latter extracts dried (MgSO$_4$) and evaporated under reduced pressure to furnish the title compound (1.6 g) as a white solid. Rf 0.67 (SS 13). Found: C,57.86; E,5.99; N,13.52. C$_{14}$H$_{17}$N$_3$O$_4$ requires C,57.72; E,5.88; N,14.42%.

PREPARATION 13

3-(2-Cyano-4-pyridyl)-(S)-alanine

Trifluoroacetic acid (10 ml) was added dropwise to a stirred, ice-cooled solution of N-t-butoxycarbonyl-3-(2-cyano-4-pyridyl)-(S)-alanine (Preparation 12; 1.6 g 5.5 mmol) in dichloromethane (10 ml) and the resulting solution stirred for 3 hours at the same temperature then evaporated under reduced pressure. The residue was dissolved in water (5 ml) and the pH of the solution adjusted to 7 with 1M aqueous sodium hydroxide solution before purification by ion-exchange chromatography on Bio Rad AG50W X-8 (H$^+$ form) resin, using an elution gradient of pyridine:water (0:100 to 10:90), to give the title compound (1.0 g) as a white solid. Rf 0.17 (SS 13), m/e 192.

PREPARATION 14

N-(2-Trifluoroacetyl-1,2,3,4-tetrahydroisoquinoline-7-sulphonyl)-3-cyano-(S)-phenylalanine Trimethylsilyl chloride (2.85 g, 26.2 mmol) was added to a stirred suspension of 3-cyano-(S)-phenylalanine (Preparation 8; 2.0 g, 10.5 mmol), N-ethyldiisopropylamine (4.1 g, 31.7 mmol) and dry dichloromethane (25 ml) and the resulting mixture heated under reflux for 2 hours. 2-Trifluoroacetyl-1,2,3,4-tetrahydroisoquinoline-7-sulphonyl chloride (Preparation 1; 3.8 g, 11.6 mmol) was then added and heating under reflux continued for a further 2 hours before removal of the solvent under reduced pressure. The residue was partitioned between ethyl acetate and water, then the organic phase washed successively with water, 1M aqueous citric acid solution and saturated brine, dried (MgSO$_4$) and evaporated under reduced pressure to give a foam (5.5 g) which, on addition of ethyl acetate (50 ml) and heating under reflux, followed by filtration of the cool suspension, afforded the title compound (1.6 g) as a white solid. Rf 0.10 (SS 14). [α]$_D^{25}$ −16.0° (c=0.1, CH$_3$OH). Found: C,52.38; H,3.68; N,8.55. C$_{21}$H$_{18}$F$_3$N$_3$O$_5$S requires C,52.38; H,3.77; N,8.73%.

A second crop (1.4 g) of product was obtained by addition of hexane to the ethyl acetate mother-liquor, then a third crop (1.1 g) obtained by chromatographic purification on silica gel of the residue obtained by evaporation under reduced pressure of the mother-liquor, using an elution gradient of hexane:dichloromethane (50:50 to 0:100) followed by dichloromethane:methanol:glacial acetic acid (98:1:1 to 97:2:1).

PREPARATION 15

N-(2-Trifluoroacetyl-1,2,3,4-tetrahydroisoquinoline-7-sulphonyl)-3-(2-cyano-4-pyridyl)-(S)-alanine The title compound was obtained from 2-trifluoroacetyl-1,2,3,4-tetrahydroisoquinoline-7-sulphonyl chloride (Preparation 1) and 3-(2-cyano-4-pyridyl)-(S)-alanine (Preparation 13), using the procedure described in Preparation 14, as a foam. Rf 0.20 (SS 13). m/e 483.

PREPARATION 16

N-(2-Trifluoroacetyl-1,2,3,4-tetrahydroisoquinoline-6-sulphonyl)-3-cyano-(S)-phenylalanine The title compound was obtained from 2-trifluoroacetyl-1,2,3,4-tetrahydroisoquinoline-6-sulphonyl chloride (Preparation 2) and 3-cyano-(S)-phenylalanine (Preparation 8), using the procedure described in Preparation 14, as a white foam. Rf 0.30 (SS 14). m/e 499 (M+NH$_4$)$^+$.

PREPARATION 17

N-(3-Trifluoroacetyl-2,3,4,5-tetrahydro-1H-3-benzazepine-7-sulphonyl)-3-cyano-(S)-phenylalanine The title compound was obtained from 3-trifluoroacetyl-2,3,4,5-tetrahydro-1H-3-benzazepine-7-sulphonyl chloride (Preparation 3) and 3-cyano-(S)-phenylalanine (Preparation

PREPARATION 18

N-(1(R,S)-Methoxymethyl-2-trifluoroacetyl-1,2,3,4-tetrahydroisoquinoline-7-sulphonyl)-3-cyano-(S)-phenylalanine The title compound was obtained from 1(R,S)-methoxymethyl-2-trifluoroacetyl-1,2,3,4-tetrahydroisoquinoline-7-sulphonyl chloride (Preparation 4) and 3-cyano-(S)-phenylalanine (Preparation 8), using the procedure described in Preparation 14, as a white solid. Rf 0.43 (SS 3).

PREPARATION 19

N-[1(R,S)-N,N-Dimethylcarbamoylmethyl)-2-trifluoroacetyl-1,2,3,4-tetrahydroisoquinoline-7-sulphonyl -3-cyano-(S)-phenylalanine The title compound was obtained from 1(R,S)-(N,N-dimethylcarbamoylmethyl)-2-trifluoroacetyl-1,2,3,4-tetrahydroisoquinoline-7-sulphonyl chloride (Preparation 5) and 3-cyano-(S)-phenylalanine (Preparation 8), using the procedure described in Preparation 14, as a white foam. Rf 0.35 (SS 16). m/e 567 $(M+H)^+$.

PREPARATION 20

N-(5-Methyl-2-trifluoroacetyl-1,2,3,4-tetrahydroisoquinoline-8-sulphonyl)-3-cyano-(S)-phenylalanine The title compound was obtained from 5-methyl-2-trifluoroacetyl-1,2,3,4-tetrahydroisoquinoline-8-sulphonyl chloride (Preparation 6) and 3-cyano-(S)-phenylalanine (Preparation 8), using the procedure described in Preparation 14, as a yellow foam. Rf 0.50 (SS 3). Found: C,53.56; H,4.45; N,8.11. $C_{22}H_{20}F_3N_3O_5S$ requires C,53.33; E,4.07; N,8.48%.

PREPARATION 21

N-(2-Trifluoroacetyl-1,2,3,4-tetrahydroisoquinoline-7-sulphonyl)-3-cyano-(S)-phenylalanine ethyl ester 2-Trifluoroacetyl-1,2,3,4-tetrahydroisoquinoline-7-sulphonyl chloride (Preparation 1; 7.72 g, 23.6 mmol) was added to a stirred, ice-cooled solution of 3-cyano-(S)-phenylalanine ethyl ester hydrochloride (Preparation 9; 6.0 g, 23.6 mmol) and N-methylmorpholine (5.0 g, 49.5 mmol) in dichloromethane (130 ml). After 18 hours at room temperature the reaction mixture was washed successively with water, 5% aqueous citric acid solution, water and saturated brine, dried (MgSO$_4$) and evaporated under reduced pressure to give an oil which was dissolved in the minimum volume of dichloromethane. Treatment of this solution with diisopropyl ether provided the title compound (11.7 g) as a gum. Rf 0.56 (SS 8). m/e 510.

PREPARATION 22

N-(2-Trifluoroacetyl-1,2,3,4-tetrahydroisocauinoline-7-sulphonyl)-3-cyano-(R,S)-phenylalanine ethyl ester The title compound was obtained from 2-trifluoroaectyl-1,2,3,4-tetrahydroisoquinoline-7-sulphonyl chloride (Preparation 1) and 3-cyano-(R,S)-phenylalanine ethyl ester (Preparation 7), using the procedure described in Preparation 21, as a white solid (after crystallisation from a mixture of diisopropyl ether and ethyl acetate), m.p. 114° C. Rf 0.50 (SS 8). Found: C,54.56; H,4.08; N,8.19. $C_{23}H_{22}F_3N_3O_5S$ requires C,54.22; H,4.35; N,8.25%.

PREPARATION 23

N-(1,2,3,4-Tetrahydroisoquinoline-7-sulphonyl)-3-cyano-(S)-phenylalanine ethyl ester A solution of sodium carbonate (11.5 g, 108.5 mmol) in water (115 ml) was added to a stirred solution of N-(2-trifluoroacetyl-1,2,3,4-tetrahydroisoquinoline-7-sulphonyl)-3-cyano-(S)-phenylalanine ethyl ester (Preparation 21; 11.5 g, 22.6 mmol) in ethanol (115 ml) and the resulting mixture stirred for 3 hours at room temperature. The bulk of the ethanol was then removed under reduced pressure, water added and the resulting suspension extracted with dichloromethane. The organic extract was washed with saturated brine, dried (MgSO$_4$) and evaporated under reduced pressure, then the residue dissolved in the minimum volume of dichloromethane. Dilution of this solution with ethanol, followed by concentration and overnight standing of the mixture, provided the title compound as a white solid (6.4 g), after filtration and washing with ether. Rf 0.26 (SS 6). m/e 414 $(M+H)^+$.

PREPARATION 24

N-(1,2,3,4-Tetrahydroisoquinoline-7-sulphonyl)-3-cyano-(R,S)-phenylalanine ethyl ester The title compound was obtained from N-(2-trifluoroacetyl-1,2,3,4-tetrahydroisoquinoline-7-sulphonyl)-3-cyano-(R,S)-phenylalanine ethyl ester (Preparation 22), using the procedure described in Preparation 23, as a white solid, m.p. 170° C. Rf 0.25 (SS 6). Found: C,60.86; H,5.49; N,9.98. $C_{21}H_{23}N_3O_4S$ requires C,61.00; H,5.61; N,10.16%:

PREPARATION 25

N-[2-(2-Propyl)-1,2,3,4-tetrahydroisoquinoline-7-sulphonyl]-3-cyano-(S)-phenylalanine ethyl ester A stirred mixture of N-(1,2,3,4-tetrahydroisoquinoline-7-sulphonyl)-3-cyano-(S)-phenylalanine ethyl ester (Preparation 23; 1.3 g, 3.14 mmol), 2-iodopropane (641 mg, 377 μl, 3.77 mmol), potassium carbonate (650 mg, 4.7 mmol) and acetonitrile (50 ml) was heated under reflux for 9 hours, more 2-iodopropane (35 μl) added and heating under reflux continued for 1 hour. The solvent was evaporated under reduced pressure and the residue purified by chromatography on silica gel, using a 0–5% methanol in dichloromethane elution gradient, followed by trituration with diisopropyl ether, to afford the title compound (1.07 g) as a white solid, m.p. 110° C. Rf 0.49 (SS 6). Found: C,63.19; H,6.34; N,8.89. $C_{24}H_{29}N_3O_4S$ requires C,63.27; H,6.41; N,9.22%.

PREPARATION 26

N-(2-Methyl-1,2,3,4-tetrahydroisoquinoline-7-sulphonyl)-3-cyano-(S)-phenylalanine ethyl ester Aqueous formaldehyde solution (370 w/v, 3.15 ml, 42 mmol) was added to a stirred solution of N-(1,2,3,4-tetrahydroisoquinoline-7-sulphonyl)-3-cyano-(S)-phenylalanine ethyl ester (Preparation 23; 3.5 g, 8.5 mmol) in dichloromethane (100 ml). After 1 hour, sodium triacetoxyborohydride (566 mg, 2.67 mmol) was added and stirring continued for 2 hours. The reaction mixture was then washed with saturated aqueous sodium bicarbonate solution, dried (MgSO$_4$) and evaporated under reduced pressure to furnish the title compound (3.6 g) as a white foam. Rf 0.83 (SS 3). m/e 428 $(M+H)^+$.

PREPARATION 27

N-(2-Methyl-1,2,3,4-tetrahydroisoquinoline-7-sulphonyl)-3-cyano-(R S)-phenylalanine ethyl ester The title compound was obtained from N-(1,2,3,4-tetrahydroisoquinoline-7-sulphonyl)-3-cyano-(R,S)-phenylalanine ethyl ester (Preparation 24), using the procedure described in Preparation 26, as a gum. Rf 0.30 (SS 6).

PREPARATION 28

N-[2-(2-Propyl)-1,2,3,4-tetrahydroisoquinoline-7-sulphonyl]-3-cyano-(S)-phenylalanine 1M Aqueous sodium hydroxide solution (6.0 ml, 6 mmol) was added to a stirred solution of N-[2-(2-propyl)-1,2,3,4-tetrahydroisoquinoline-7-sulphonyl]-3-cyano-(S)-phenylalanine ethyl ester (Preparation 25; 1.0 g, 2.19 mmol) in 1,4-dioxan (6.0 ml). After 2.5 hours at room temperature, the reaction mixture was neutralised using 1M hydrochloric acid (6.0 ml) and evaporated to dryness under reduced pressure. The residue was extracted successively with dichloromethane and a mixture of dichloromethane:2-propanol (9:1), then the combined extracts evaporated under reduced pressure to provide a material which, on trituration with ether, gave the title compound as a white powder (780 mg). Rf 0.06 (SS 3). m/e 428 (M+H)$^+$

PREPARATION 29

N-(2-Methyl-1,2,3,4-tetrahydroisoquinoline-7-sulphonyl)-3-cyano-(S)-phenylalanine The title compound was obtained from N-(2-methyl-1,2,3,4-tetrahydroisoquinoline-7-sulphonyl)-3-cyano-(S)-phenylalanine ethyl ester (Preparation 26), using the procedure described in Preparation 28, as a white powder. Rf 0.15 (SS 3). m/e 400 (M+H)$^+$.

PREPARATION 30

N-(2-Methyl-1,2,3,4-tetrahydroisoquinoline-7-sulphonyl)-3-cyano-(R,S)phenylalanine The title compound was obtained from N-(2-methyl-1,2,3,4-tetrahydroisoquinoline-7-sulphonyl)-3-cyano-(R,S)-phenylalanine ethyl ester (Preparation 27), using the procedure described in Preparation 28, as a white solid, m.p. 143°–145° C. (decomp.) after crystallisation from acetonitrile. Rf 0.35 (SS 13). Found: C,58.77; H,5.29; N,10.73. $C_{20}H_{21}N_3O_4S$; 0.50 $H_2O$; 0.25 $CH_3CN$ requires C,58.79; H,5.48; N,10.87%.

PREPARATION 31

4(R)-Methylpiperidine-2(R)-carboxylic acid ethyl ester

The title compound was obtained by the method described in Biochem. Biophys. Res. Comm., 1981, 101, 440.

PREPARATION 32

4-Methyl-1,2,3,6-tetrahydropyridine-2(R)-carboxylic acid ethyl ester hydrochloride (a) 4-Methyl-1-[1(S)-phenylethyl]-1,2,3,6-tetrahydropyridine-2(R)-carboxylic acid ethyl ester This intermediate was obtained by the method described in Tetrahedron:Asymmetry, 1991 2, 1263.

(b)

A stirred solution of the above intermediate (13.56 g, 49.7 mmol) in toluene (150 ml), under nitrogen, was heated under reflux for 2 hours, using a Dean-Stark trap. 1,8-Bis(dimethylamino)naphthalene (1.08 g, 5.0 mmol) was then added, heating continued for a further 1 hour, the reaction mixture allowed to cool and the Dean-Stark trap removed. After the addition of 1-chloroethyl chloroformate (10.7 ml, 14.2 g, 99.5 mmol), the reaction mixture was stirred under reflux for 16 hours, allowed to cool, treated with absolute ethanol (80 ml), stirred under reflux for 2 hours more and evaporated under reduced pressure. The residue was partitioned between ethyl acetate (100 ml) and 1M hydrochloric acid (50 ml), then the aqueous phase separated, neutralised with solid sodium bicarbonate and extracted with dichloromethane (3×200 ml). Evaporation under reduced pressure of the dried (MgSO$_4$), combined extracts provided a brown residue which was purified by chromatography on silica gel, using a 0–5% methanol in dichloromethane elution gradient, and then converted to the required hydrochloride salt using excess ethereal hydrogen chloride. The product was further purified by dissolution in dichloromethane (20 ml), filtration (to remove residual silica gel), dilution of the filtrate with ether (200 ml), filtration, washing of the precipitate with ether and drying in vacuo. A sample of this purified product (5.77 g) was crystallised from a mixture of ether and ethanol to afford the title compound as white crystals, m.p. 110°–111° C. Rf 0.35 (SS 3). $[\alpha]_D^{25}$+113.7° (c=1.0, $CH_3CH_2OH$). Found: C,52.79; H,7.94; N,6.68. $C_9H_{15}NO_2$; HCl requires C,52.55; H,7.84; N,6.81%.

PREPARATION 33

4-Methyl-1,2,3,6-tetrahydropyridine-2(R,S)-carboxylic acid ethyl ester hydrochloride (a) 1-Benzyl-4-methyl-1,2,3,6-tetrahydropyridine-2(R,S)-carboxylic acid ethyl ester This intermediate was obtained by the method described in Tetrahedron Asymmetry, 1991, 2, 1263.

(b)

The title compound (82% yield) was obtained from the intermediate of (a) above, using the method of Preparation 32(b), as a white solid, m.p. 130°–130.5° C. Rf 0.35 (SS 3).

PREPARATION 34

4-Methyl-1,2,3,6-tetrahydropyridine-2(S)-carboxylic acid ethyl ester hydrochloride (a) 1-Benzyl-4-methyl-1,2,3,6-tetrahydropyridine-2(R,S)-carboxylic acid hydrochloride A stirred solution of 1-benzyl-4-methyl-1,2,3,6-tetrahydropyridine-2(R,S)-carboxylic acid ethyl ester (Preparation 33(a); 20.1 g, 77.5 mmol) in 5M hydrochloric acid (200 ml) was heated at 100° C. for 4.5 hours and then evaporated to dryness under reduced pressure. Residual water was removed azeotropically using dichloromethane followed by toluene to give the required product (24.0 g) as a white foam, Rf 0.40 (SS 13), which was used without further purification in the next step.

(b) 1-Benzyl-4-methyl-1,2,3,6-tetrahydropyridine-2(R,S)-carboxylic acid N-acetyl-(1R,2S)-ephedrine ester 1,3-Dicyclohexylcarbodiimide (20.6 g, 0.1 mol) was added to a stirred solution of the product from (a) above (24.0 g, 89.6 mmol), N-acetyl-(1R,2S)-ephedrine (18.47 g, 89.2 mmol), obtained by the method described in J. Amer. Pharmaceut. Assoc., 1952, 41, 545, (see J. Med. Chem., 1965, 8, 466), N-ethyldiisopropylamine (12.9 g, 0.1 mmol) and 4-dimethylaminopyridine (9.51 g, 77.5 mmol) in dichloromethane (250 ml). After 3 days at room temperature, the reaction mixture was filtered and the filtrate evaporated to dryness under reduced pressure. The residue was partitioned between ethyl acetate and water, then the organic phase separated, washed with water, dried (MgSO$_4$) and evaporated under reduced pressure to give the crude product, which was purified by chromatography on silica gel, using ether as eluent, to furnish the required pure product (25.5 g)

as an oil. Rf 0.35 (SS 2). Found: C,73.34; H,7.71; N,5.73. $C_{26}H_{32}N_2O_3$; 0.30 $(C_2H_5)_2O$ requires C,73.78; H,7.91; N,6.33%.

(c) 4-Methyl-1-(2,2,2-trichloroethoxycarbonyl)-1,2,3,6-tetrahydropyridine-2(R,S)-carboxylic acid N-acetyl-(1R, 2S)-ephedrine ester Sodium bicarbonate (11.21 g, 133 mmol), then 2,2,2-trichloroethyl chloroformate (11.7 ml, 17.97 g, 84.8 mmol), were added to a stirred solution of the product from (b) above (25.48 g, 60.6 mmol) in dry dichloromethane (200 ml) and the resulting mixture was heated under reflux for 22 hours. The solvent was removed under reduced pressure and the residue partitioned between ethyl acetate and water. The separated organic phase was washed with saturated brine, dried ($MgSO_4$) and evaporated under reduced pressure, then the residue purified by chromatography on silica gel, using ether as eluent, to afford the required product (28.1 g) as a gum. Rf 0.40 (SS 2). Found: C,52.10; H,5.38; N,5.24. $C_{22}H_{27}Cl_3N_2O_5$ requires C,52.24; H,5.38; N,5.54%.

(d) 4-Methyl-1,2,3,6-tetrahydropyridine-2(R)-carboxylic acid N-acetyl-(1R,2S)-ephedrine ester and 4-methyl-1,2,3,6-tetrahydropyridine-2(S)-carboxylic acid N-acetyl-(1R,2S)-ephedrine ester 1M Aqueous potassium dihydrogen phosphate solution (40 ml, 40 mmol), then zinc dust (40 g, 610 mmol), were added to a rapidly stirred solution of the product from (c) above (32.9 g, 65 mmol) in tetrahydrofuran (200 ml). After 1 hour at room temperature, the reaction mixture was filtered and the bulk of the organic-solvent removed under reduced pressure, then the residue basified with saturated aqueous sodium bicarbonate solution and extracted with ethyl acetate. The extract was washed with saturated brine, dried ($MgSO_4$) and evaporated under reduced pressure to give an oil (21.46 g), which was chromatographed on silica gel using an elution gradient of ethanol:ethyl acetate (1:4 to 3:7), to provide firstly the 2(R)-diastereoisomeric ester (2.75 g), Rf 0.30 (SS 14), m/e 331 $(M+H)^+$, followed by the 2(S)-diastereoisomeric ester (2.90 g), Rf 0.22 (SS 14), m/e 331 $(M+H)^+$, each as a pale yellow oil.

(e) N-t-Butoxycarbonyl-4-methyl-1,2,3,6-tetrahydropyridine-2(S)-carboxylic acid N-acetyl-(1R, 2S)-ephedrine ester Di-t-butyl dicarbonate (4.4 g, 20.2 mmol) was added to a stirred solution of the 2(S)-ester product from (d) above, (5.13 g, 15.5 mmol) and N-methylmorpholine (2.04 g, 20.2 mmol) in dichloromethane (40 ml). After 5 hours at room temperature, more di-t-butyl dicarbonate (1.35 g, 6.2 mmol) was added and the reaction mixture stirred for a further 15 hours before removal of the solvent under reduced pressure. The residual mixture was partitioned between ethyl acetate and water, then the organic phase washed successively with 1M aqueous citric acid solution, saturated aqueous sodium bicarbonate solution and saturated brine, dried ($MgSO_4$) and evaporated under reduced pressure to give a gum which was purified by chromatography on silica gel, using ether as eluant, to afford the required product (6.02 g) as a gum. Rf 0.45 (SS 2). Found: C,66.84; H,7.97; N,6.50. $C_{24}H_{34}N_2O_5$ requires C,66.95; H,7.96; N,6.51%.

(f) N-t-Butoxycarbony-4-methyl-1,2,3,6-tetrahydropyridine-2(S)-carboxylic acid

1M Aqueous sodium hydroxide solution (69 ml, 69 mmol) was added to a stirred solution of the product from (e) above (5.97 g, 13.9 mmol) in 1,4-dioxan (60 ml). After 3 hours at room temperature, solid citric acid (5.53 g, 26 mmol) was added and the bulk of the solvent removed under reduced pressure. The residual suspension was basified to pH 10 with 1M aqueous sodium hydroxide solution, washed with dichloromethane, acidified to pH 3 with solid citric acid and extracted with ethyl acetate. The organic extract was washed with saturated brine, dried ($MgSO_4$) and evaporated under reduced pressure to provide the required product (3.47 g) as a gum. Rf 0.60 (SS 17).

(g) N-t-Butoxycarbonyl-4-methyl-1,2,3,6-tetrahydropyridine-2(S)-carboxylic acid ethyl ester 1,3-Dicyclohexylcarbodiimide (4.3 g, 20.8 mmol) was added to a stirred solution of the product from (f) above (3.35 g, 13.9 mmol), ethanol (4.1 ml, 69.4 mmol) and 4-dimethylaminopyridine (1.7 g, 13.9 mmol) in dichloromethane (40 ml). After 18 hours at room temperature, glacial acetic acid (0.4 ml) was added and the reaction mixture stirred for a further 0.5 hour before being filtered. The residue obtained by evaporation of the filtrate under reduced pressure was partitioned between ether and water, then the organic phase washed successively with 1M aqueous citric acid solution, saturated aqueous sodium bicarbonate solution and saturated brine, dried ($MgSO_4$) and evaporated under reduced pressure to give an oil (5.15 g), which was purified by chromatography on silica gel, using hexane:ether (4:1) as eluent, to furnish the required product (3.4 g) as a clear oil. Rf 0.30 (SS 4). m/e 270 $(M+H)^+$.

(h)

A stirred, ice-cooled solution of the product from (g) above (3.13 g, 11.62 mmol) in ethyl acetate (30 ml) was saturated with hydrogen chloride over 0.5 hour and then stood at room temperature for a further 2 hours. The solvent was evaporated under reduced pressure and the residue crystallised from a mixture of ether and ethanol to afford the title compound (2.20 g) as white crystals, m.p. 108°–109° C. Rf 0.35 (SS 3), $[\alpha]_D^{25}$ –106.5° (c=1.0, $CH_3CH_2OH$). Found: C,52.49; H,7.90; N,6.70. $C_9H_{15}NO_2$; HCl requires C,52.55; H,7.84; N,6.81%.

The compound obtained by carrying out steps (e), (f), (g) and (h) on the 2(R)-ester from (d) above was found to be identical with the title compound of Preparation 32.

PREPARATION 35

4-Ethyl-1,2,3,6-tetrahydropyridine-2(R,S)-carboxylic acid ethyl ester hydrochloride (a) 2-Cyano-4-ethyl-1-methyl-1,2,3,6-tetrahydropyridine hydrochloride Methyl iodide (74.7 ml, 170.33 g, 1.22 mol) was cautiously added portionwise to a stirred solution of 4-ethylpyridine (107.2 g, 1 mol) in acetone (500 ml), the resulting mixture heated under reflux for 2 hours and allowed to cool, then a portion of solvent (ca. 100 ml) removed under reduced pressure. Addition of ether (1.0 l), collection and washing with ether of the precipitate, followed by drying in vacuo, provided the required quaternary iodide (245 g) as a very hygroscopic solid.

6M Hydrochloric acid (130 ml) was slowly added to a stirred solution of potassium cyanide (130 g, 2.5 mol) in water (260 ml) covered by a layer of ether (400 ml), ensuring that the temperature was maintained below 15° C. Successive, portionwise addition of the above quaternary salt (139.49 g, 0.56 mol) and sodium borohydride (27 g, 0.71 mol) over 15 minutes gave a milky mixture, which was stirred at ca. 10° C. for 0.5 hour and then at room temperature for a further a hours. The ether phase was removed by suction and combined with an ether extract of the aqueous phase, then washing with saturated brine and drying ($MgSO_4$) effected. The ether solution was ice-cooled, with stirring, and methyl iodide (6 ml) added to precipitate any unwanted 4-ethyl-1-methylpiperidine as the derived quaternary iodide. Filtration, followed by treatment of the filtrate with excess 1M ethereal hydrogen chloride, afforded the required product (43.77 g) as an oil. Rf 0.20 (SS 18), which was used without further purification in the next step.

(b) 4-Ethyl-1-(2,2,2-trichloroethoxycarbonyl)-1,2,3,6-tetrahydropyridine-2(R,S)-carboxylic acid ethyl ester A stirred solution of the product from (a) above (43.5 g, 0.23 mol) in ethanol (100 ml) was saturated with hydrogen chloride, heated under reflux for 6.5 hours and then evaporated to dryness under reduced pressure. The residue was basified with aqueous sodium carbonate solution, then extraction with ethyl acetate effected. The extract was washed with saturated brine, dried (MgSO$_4$) and evaporated under reduced pressure to give the crude ethyl ester, which was partially purified by chromatography on silica gel, using hexane:ethyl acetate:diethylamine (90:5:2) as eluent, to provide an oil (8.0 g).

Sodium carbonate (10.0 g, 94 mmol) and 2,2,2-trichloroethyl chloroformate (13.0 g, 61 mmol) were added successively to a stirred solution of the above crude ester (8.0 g, 40 mmol) in dichloromethane (200 ml) and the resulting mixture heated under reflux for 20 hours, then evaporated under reduced pressure. The residue was partitioned between ethyl acetate and water, then the organic phase dried (MgSO4) and evaporated under reduced pressure to give an oil which was purified by chromatography on silica gel, using hexane:ethyl acetate(50:1) as eluent, to furnish the required product (4.8 g) as a colourless oil. Rf 0.25 (SS 19).

(c)

1M Aqueous potassium dihydrogen phosphate solution (70 ml, 70 mmol), then zinc dust (46 g, 700 mmol), were added to a rapidly stirred solution of the product from (b) above (4.76 g, 13.3 mmol) in tetrahydrofuran (220 ml). After 2 hours at room temperature more zinc dust (5 g, 76 mmol) was added and the reaction mixture stirred for a further hour before being filtered. The filter pad was washed with water and tetrahydrofuran, then the bulk of the organic solvent removed from the combined filtrate and washings. The residual mixture was acidified with 2M hydrochloric acid (30 ml), washed with ethyl acetate to remove starting material (2.32 g recovered), neutralised with solid potassium carbonate and extracted with dichloromethane. The combined organic extracts were washed with saturated brine, dried (MgSO$_4$), treated with excess ethereal hydrogen chloride and evaporated under reduced pressure. Purification of the residue by chromatography on silica gel, using dichloromethane:methanol (95:5) as eluent, furnished the title compound (330 mg), as a colourless waxy solid. m/e 184 (M+H)$^+$.

PREPARATION 36

4-Methyl-1-[N-(2-trifluoroacetyl-1,2,3,4-tetrahydroisoquinoline-7-sulphonyl)-3-cyano-(S)-phenylalanyl]-1,2,3,6-tetrahydropyridine-2(R)-carboxylic acid ethyl ester Oxalyl chloride (3.10 g, 24.4 mmol) was added dropwise to a stirred, ice-cooled suspension of N-(2-trifluoroacetyl-1,2,3,4-tetrahydroisoquinoline-7-sulphonyl)-3-cyano-(S)-phenylalanine (Preparation 14; 2.93 g, 6.08 mmol) in dichloromethane (20 ml), followed by dimethylformamide (1 drop). After 2 hours at room temperature, the reaction solvent was evaporated under reduced pressure and the residual oxalyl chloride removed azeotropically, using dichloromethane (x2) followed by toluene, to produce the crude acyl chloride hydrochloride as an oil which was then dissolved in dichloromethane (50 ml).

To this stirred, ice-cooled solution were added, successively, 4-methyl-1,2,3,6-tetra-hydropyridine-2(R)-carboxylic acid ethyl ester hydrochloride (Preparation 32; 1.37 g, 6.67 mmol) and N-ethyldiisopropylamine (1.72 g, 13.3 mmol). The resulting solution was kept at about 0° C. for 18 hours and then evaporated under reduced pressure. The residue was dissolved in ethyl acetate, then the solution washed successively with water, 1M hydrochloric acid, saturated aqueous sodium bicarbonate solution and saturated brine, dried (MgSO$_4$) and evaporated under reduced pressure to give the crude product, which was purified by chromatography on silica gel, using an ethyl acetate in hexane elution gradient, to afford the title compound (3.43 g) as a white foam. Rf 0.42 (SS 20). $[\alpha]_D^{25}$ +23° (c=0.1CH$_3$OH).

Found: C,56.70; H,4.75; N,8.68. C$_{30}$H$_{31}$F$_3$N$_4$O$_6$S requires C,56.95; H,4.94; N,8.85%.

The title compounds of Preparation 37–44 were obtained by analogy with Preparation 36 by coupling the appropriate amino acid and amine precursors.

PREPARATION 37

4-Methyl-1-[N-(2-trifluoroacetyl-1,2,3,4-tetrahydroisoquinoline-7-sulphonyl)-3-(2-cyano-4-pyridyl)-(S)-alanyl]-1,2,3,6-tetrahydropyridine-2(R)-carboxylic acid ethyl ester Obtained from Preparation 15 and Preparation 32 as a foam. Rf 0.21 (SS 12). Found: C,54.65; H,4.89; N,10.69. C$_{29}$H$_{30}$F$_3$N$_5$O$_6$S requires C,54.96; H,4.77; N,11.05%.

PREPARATION 38

4-Methyl-1-[N-(2-trifluoroacetyl-1,2,3,4-tetrahydroisoquinoline-6-sulphonyl)-3-cyano-(S)-phenylalanyl]-1,2,3,6-tetrahydropyridine-2(R)-carboxylic acid ethyl ester Obtained from Preparation 16 and Preparation 32. Rf 0.35 (SS 6). Found: C,56.58; H,5.10; N,8.84. C$_{30}$H$_{31}$F$_3$N$_4$O$_6$S requires C,56.95; H,4.94; N,8.86%.

PREPARATION 39

4-Methyl-1-[N-(3-trifluoroacetyl-2,3,4,5-tetrahydro-1H-3-benzazepine-7-sulphonyl)-3-cyano-(S)-phenylalanyl-1,2,3,6-tetrahydropyridine-2(R)-carboxylic acid ethyl ester Obtained from Preparation 17 and Preparation 32 as a white foam. Rf 0.25 (SS 21). m/e 647 (M+H)$^+$.

PREPARATION 40

1-[N-(1(RS)-Methoxymethyl-2-trifluoroacetyl-1,2,3,4-tetrahydroisoquinoline-7-sulphonyl)-3-cyano-(S)-]phenylalanyl]-4-methyl-1,2,3,6-tetrahydropyridine-2(R)-carboxylic acid ethyl ester Obtained from Preparation 18 and Preparation 32 as a white foam. Rf 0.35 (SS 8). Found: C,56.60; H,5.03; N,8.13. C$_{32}$H$_{35}$F$_3$N$_4$O$_7$S requires C,56.30; H,5.21; N,8.28%.

PREPARATION 41

1-{N-[1(R,S)-(N,N-Dimethylcarbamoylmethyl)-2-trifluoroacetyl-1,2,3,4-tetrahydroisoquinoline-7-sulphonyl]-3-cyano-(S)-phenylalanyl}-4-methyl-1,2,3,6-tetrahydropyridine-2(R)-carboxylic acid ethyl ester Obtained from Preparation 19 and Preparation 32 as a white foam. Rf 0.40 (SS 22). Found: C,56.53; H,5.22; N,9.54. C$_{34}$H$_{38}$F$_3$N$_5$O$_7$S requires C,56.90; H,5.34; N,9.76%.

PREPARATION 42

4-Methyl-1-[N-(5-methyl-2-trifluoroacetyl-1,2,3,4-tetrahydroisoquinoline-8-sulphonyl)-3-cyano-(S)- phenylalanyl]-1,2,3,6-tetrahydropyridine-2(R)-carboxylic acid ethyl ester

Obtained from Preparation 20 and Preparation 32 as a yellow foam. Rf 0.60 (SS 8). Found : C,57.32; H,5.28; N,8.16. $C_{31}H_{33}F_3N_4O_6S$; 0.50 $CH_3CO_2CH_2CH_3$ requires C,57.38; H,5.40; N,8.11%.

PREPARATION 43

4-Methyl-1-[N-(2-trifluoroacetyl-1,2,3,4-tetrahydroisoquinoline-7-sulphonyl)-3-cyano-(S)-phenylalanyl]-1,2,3,6-tetrahydropyridine-2(R,S)-carboxylic acid ethyl ester Obtained from Preparation 14 and Preparation 33. Rf 0.42 (SS 20). Found: C,56.72; H,4.77; N,8.71. $C_{30}H_{31}F_3N_4O_6S$ requires C,56.95; H,4.94; N,8.85%.

PREPARATION 44

4-Ethyl-1-[N-(2-trifluoroacetyl-1,2,3,4-tetrahydroisoquinoline-7-sulphonyl)-3-cyano-(S)-phenylalanyl]-1,2,3,6-tetrahydropyridine-2(R,S)-carboxylic acid ethyl ester Obtained from Preparation 14 and Preparation 35 as a colourless foam. Rf 0.53 (SS 8). m/e 664.6 $(M+NH_4)^+$.

PREPARATION 45

4-Methyl-1-[N-(1,2,3,4-tetrahydroisoquinoline-7-sulphonyl)-3-cyano-(S)-phenylalanyl]-1,2,3,6-tetrahydropyridine-2(R)-carboxylic acid ethyl ester A solution of sodium carbonate (2.83 g, 26.7 mmol) in water (20 ml) was added to a stirred solution of 4-methyl-1-[N-(2-trifluoroacetyl-1,2,3,4-tetrahydroisoquinoline-7-sulphonyl)-3-cyano-(S)-phenylalanyl]-1,2,3,6-tetrahydropyridine-2(R)-carboxylic acid ethyl ester (Preparation 36; 3.38 g, 5.34 mmol) in ethanol (20 ml) and the resulting suspension stirred for 20 hours. The bulk of the ethanol was removed under reduced pressure, the residual mixture diluted with water and extraction with ethyl acetate effected. The organic extract was washed with water, then saturated brine, dried ($MgSO_4$) and evaporated under reduced pressure to afford the title compound (2.29 g) as a foam. Rf 0.42 (SS 9). $[\alpha]_D^{25}+14°$ (c=0.1, $CH_3OH$). Found: C,61.60; H,6.06; N,10.10. $C_{28}H_{32}N_4O_5S$; 0.50 $H_2O$ requires C,61.63; H,6.09; N,10.26%.

The title compounds of Preparations 46–52 were obtained from their trifluoroacetyl precursors, Preparations 37–42 and 44 respectively, using the procedure described in Preparation 46.

PREPARATION 46

4-Methyl-1-[N-(1,2,3,4-tetrahydroisoquinoline-7-sulphonyl)-3-(2-cyano-4-pyridyl)-(S)-alanyl]-1,2,3,6-tetrahydropyridine-2(R)-carboxylic acid ethyl ester Obtained from Preparation 37 as a foam. Rf 0.41 (SS 13). m/e 538 $(M+H)^+$. Found: C,59.45; H,5.95; N,12.47. $C_{27}H_{31}N_5O_5S$ requires C,60.31; H,5.81; N,13.02%.

PREPARATION 47

4-Methyl-1-[N-(1,2,3,4-tetrahydroisoquinoline-6-sulphonyl)-3-cyano-(S)-phenylalanyl]-1,2,3,6-tetrahydropyridine-2(R)-carboxylic acid ethyl ester Obtained from Preparation 38 as a white foam. Rf 0.50 (SS 9). m/e 537 $(M+H)^+$.

PREPARATION 48

4-Methyl-1-[N-(2,3,4,5-tetrahydro-1H-3-benzazenine-7-sulphonyl)-3-cyano-(S)-phenylalanyl]-1,2,3,6-tetrahydropyridine-2(R)-carboxylic acid ethyl ester Obtained from Preparation 39 as a white foam. Rf 0.28 (SS 3). m/e 551 $(M+H)^+$.

PREPARATION 49

1-[N-(1(R,S)-Methoxymethyl-1,2,3,4-tetrahydroisoquinoline-7-sulphonyl)-3-cyano-(S)-phenylalanyl]-4-methyl-1,2,3,6-tetrahydropyridine-2(R)-carboxylic acid ethyl ester Obtained from Preparation 40 as a white foam. Rf 0.18 (SS 6). m/e 581 $(M+H)^+$.

PREPARATION 50

2-{N-[1(R,S)-(N,N-Dimethylcarbamoylmethyl)-1,2,3,4-tetrahydroisoquinoline-7-sulphonyl]-3-cyano-(S)-phenylalanyl}-4-methyl-1,2,3,6-tetrahydropyridine-1(R)-carboxylic acid ethyl ester Obtained from Preparation 41 as a white foam. Rf 0.15 (SS 6). m/e 622 $(M+H)^+$.

PREPARATION 51

4-Methyl-1-[N-(5-methyl-1,2,3,4-tetrahydroisoquinoline-8-sulphonyl)-3-cyano-(S)-phenylalanyl]-1,2,3,6-tetrahydropyridine-2(R)-carboxylic acid ethyl ester Obtained from Preparation 42 as a white foam. Rf 0.40 (SS 3). m/e 551 $(M+H)^+$.

PREPARATION 52

4-Ethyl-1-[N-(1,2,3,4-tetrahydroisoquinoline-7-sulphonyl)-3-cyano-(S)-phenylalanyl]-1,2,3,6-tetrahydropyridine-2(R,S)-carboxylic acid ethyl ester Obtained from Preparation 44 as a colourless foam. Rf 0.13 (SS 23). m/e 551.3 $(M+H)^+$.

PREPARATION 53

4-Methyl-1-[N-(2-methyl-1,2,3,4-tetrahydroisoquinoline-7-sulphonyl)-3-cyano-(S)-phenylalanyl]-1,2,3,6-tetrahydropyridine-2(R)-carboxylic acid ethyl ester Aqueous formaldehyde solution (37% w/v, 1.4 ml, 17.3 mmol) was added to a stirred solution of 4-methyl-1-[N-(1,2,3,4-tetrahydroisoquinoline-7-sulphonyl)-3-cyano-(S)-phenylalanyl]-1,2,3,6-tetrahydropyridine-2(R)-carboxylic acid ethyl ester (Preparation 45; 2.26 g, 4.2 mmol) in dichloromethane (30 ml). After 0.75 hour, sodium triacetoxyborohydride (1.34 g, 6.32 mmol) was added and stirring continued for 4 hours. The reaction mixture was then washed successively with saturated aqueous sodium bicarbonate solution and saturated brine, dried ($MgSO_4$) and evaporated under reduced pressure, then the residue purified by chromatography on silica gel, using ethyl acetate: diethylamine (98:2) as eluent, to provide the title compound (2.15 g) as a foam. $[\alpha]_D^{25}+9°$ (c=0.1, $CH_3OH$). Found: C,62.81; H,6.28; N,9.53. $C_{29}H_{34}N_4O_5S$; 0.30 $H_2O$ required C,62.63; H,6.27; N,10.07%.

The title compounds of Preparations 54–60 were obtained from their corresponding precursors, Preparations 46–52 respectively, using the procedure described in Preparation 53.

PREPARATION 54

4-Methyl-1-[N-(2-methyl-1 2,3,4-tetrahydroisoquinoline-7-sulphonyl)-3-(2-cyano-4-pyridyl)-(S)-alanyl]-1,2,3,6-tetrahydropyridine-2(R)-carboxylic acid ethyl ester Obtained from Preparation 46 as a foam. Rf 0.36 (SS 13). m/e 552 $(M+H)^+$. Found : C,61.52; H,5.94; N,11.78. $C_{28}H_{33}N_5O_5S$ requires C,60.96; H,6.03; N,12.69%.

PREPARATION 55

4-Methyl-1-[N-(2-methyl-1 2,3,4-tetrahydroisoquinoline-6-sulphonyl)-3-cyano-(S)-phenylalanyl]-1,2,3,6-tetrahydropyridine-2(R)-carboxylic acid ethyl ester Obtained from Preparation 47 as a white solid. Rf 0.30 (SS 6). Found: C,63.31; H,6.22; N,10.17. $C_{29}H_{34}N_4O_5S_2$ requires C,63.25; H,6.09; N,10.12%.

PREPARATION 56

4-Methyl-1-[N-(3-methyl-2,3,4,5-tetrahydro-1H-3-benzazepine-7-sulphonyl-3-cyano-(S)-phenylalanyl]-1,2,3,6-tetrahydropyridine-2(R)-carboxylic acid ethyl ester Obtained from Preparation 48 as a white foam. Rf 0.30 (SS 3). m/e 565 $(M+H)^+$.

PREPARATION 57

1-[N-(1(R,S)-Methoxymethyl-2-methyl-1,2,3,4-tetrahydroisoquinoline-7-sulphonyl)-3-cyano-(S)-phenylalanyl]-4-methyl-1,2,3,6-tetrahydropyridine-2(R)-carboxylic acid ethyl ester Obtained from Preparation 49 as a white foam. Rf 0.22 (SS 6). m/e 595 $(M+H)^+$.

PREPARATION 58

1-{N-[1(R,S)-(N,N-Dimethylcarbamoylmethyl-2-methyl-1,2,3,4-tetrahydroisoquinoline-7-sulphonyl]-3-cyano-(S)-phenylalanyl}-4-methyl-1,2,3,6-tetrahydropyridine-2(R)-carboxylic acid ethyl ester Obtained from Preparation 50 as a white foam. Rf 0.23 (SS 6). m/e 636 $(M+H)^+$.

PREPARATION 59

4-Methyl-1-[N-(2,5-dimethyl-1,2,3,4-tetrahydroisoquinoline-8-sulphonyl)-3-cyano-(S)-phenylalanyl]-1,2,3,6-tetrahydropyridine-2(R)-carboxylic acid ethyl ester Obtained from Preparation 51 as a gum. Rf 0.51 (SS 3). m/e 565 $(M+H)^+$.

PREPARATION 60

4-Ethyl-1-[N-(2-methyl-1,2,3,4-tetrahydroisoquinoline-7-sulphonyl)-3-cyano-(S)-phenylalanyl]-1,2,3,6-tetrahydropyridine-2(R,S)-carboxylic acid ethyl ester Obtained from Preparation 52 as a colourless foam. Rf 0.25 (SS 23). Found: C,63.77; H,6.51; N,9.85. $C_{30}H_{36}N_4O_5S$ requires C,63.83; H,6.38;, N,9.33%.

PREPARATION 61

4-Methyl-1-{N-[3-(2-propyl)-2,3,4,5-tetrahydro-1H-3-benzazepine-7-sulphonyl]-3-cyano-(S)-phenylalanyl}-1,2,3,6-tetrahydropyridine-2(R)-carboxylic acid ethyl ester A stirred mixture of 4-methyl-1-[N-(2,3,4,5-tetrahydro-1H-3-benzazepine-7-sulphonyl-3-cyano-(S)-phenylalanyl]-1,2,3,6-tetrahydropyridine-2(R)-carboxylic acid ethyl ester (Preparation 48; 550 mg, 1 mmol), 2-iodopropane (204 mg, 120 µl, 1.2 mmol), anhydrous potassium carbonate (207 mg, 1.5 mmol) and acetonitrile (20 ml) was heated under reflux for 6 hours, more 2-iodopropane (60 µl, 0.6 mmol) added, then heating continued for a further 3.5 hours. The cool reaction mixture was filtered, the filtrate evaporated under reduced pressure and the residue chromatographed on silica gel, using dichloromethane:methanol:0.880 aqueous ammonia solution (95:5:0.5) as eluent, to provide the title compound (400 mg) as a white foam. Rf 0.29 (SS 6). m/e 593 $(M+H)^+$.

The title compounds of Preparations 62 and 63 were obtained by analogy with Preparation 61 from their corresponding amine precursors and the appropriate alkylating agent.

PREPARATION 62

1-{N-[3-(3-Dimethylamino-1-propyl)-2,3,4,5-tetrahydro-1H-3-benzazepine-7-sulphonyl]-3-cyano-(S)-phenylalanyl}-4-methyl-1,2,3,6-tetrahydropyridine-2(R)-carboxylic acid ethyl ester Obtained from Preparation 48 and 3-dimethylamino-1-propyl chloride hydrochloride as a white foam. Rf 0.33 (SS 9). m/e 636 $(M+H)^+$.

PREPARATION 63

1-[N-(2-Benzyl-1,2,3,4-tetrahydroisoquinoline-7-sulphonyl)-3-cyano-(S)-phenylalanyl]-4-methyl-1,2,3,6-tetrahydropyridine-2(R)-carboxylic acid ethyl ester Obtained from Preparation 45 and benzyl bromide as a white foam. Rf 0.78 (SS 6). m/e 627 $(M+H)^+$.

The title compounds of Preparations 64–66 were obtained by analogy with Preparation 36 by coupling the appropriate amino acid and amine precursors.

PREPARATION 64

4-Methyl-1-[N-(2-methyl-1,2,3,4-tetrahydroisoquinoline-7-sulphonyl)-3-cyano-(S)-phenylalanyl]-1,2,3,6-tetrahydropyridine-2(S)-carboxylic acid ethyl ester Obtained from Preparation 29 and Preparation 34 as a white foam. Rf 0.50 (SS 6). m/e 551 $(M+H)^+$.

PREPARATION 65

4-Methyl-1-{N-[2-(2-propyl)-1 2,3,4-tetrahydroisoquinoline-7-sulphonyl]-3-cyano-(S)-phenylalanyl}-1,2,3,6-tetrahydropyridine-2(R)-carboxylic acid ethyl ester Obtained from Preparation 28 and Preparation 32 as a white foam. Rf 0.30 (SS 6). m/e 579 $(M+H)^+$.

PREPARATION 66

4(R)-Methyl-1-[N-(2-methyl-1,2,3,4-tetrahydroisoquinoline-7-sulphonyl)-3-cyano-(R,S)-phenylalanyl]piperidine-2(R)-carboxylic acid ethyl ester Obtained from Preparation 30 and Preparation 31 as a white foam. Rf 0.34 and 0.42 (SS 6).

PREPARATION 67

4-Methyl-1-[N-(2-methyl-1,2,3,4-tetrahydroisoquinoline-7-sulphonyl)-3-amidino-(S)-phenylalanyl]-1,2,3,6-tetrahydropyridine-2(R)-carboxylic acid ethyl ester hydrochloride A stirred, ice-cooled solution of 4-methyl-1-[N-(2-methyl-1,2,3,4-tetrahydroisoquinoline-7-sulphonyl)-3-cyano-(S)-phenylalanyl]-1,2,3,6-tetrahydropyridine-2(R)-carboxylic acid ethyl ester (Preparation 53; 2.12 g, 3.85 mmol) in dry ethanol (25 ml) was saturated with hydrogen chloride, refrigerated for 68 hours and then evaporated under reduced pressure. The residue was dissolved in dichloromethane, the solution evaporated under reduced pressure and the remaining residue dissolved in dry ethanol (25 ml). This solution was cooled in an ice-salt bath, with stirring, saturated with ammonia and heated under reflux for 2 hours. The reaction mixture was evaporated under reduced pressure, the residue dissolved in water and the solution washed with ether, saturated with sodium chloride and extracted with dichloromethane. Evaporation under reduced pressure of the dried (MgSO$_4$) extract gave the title compound (2.05 g) as a white solid. $[\alpha]_D^{25}$+30° (c=0.1, CH$_3$OH). Found: C,54.98; H,6.49; N,10.94. C$_{29}$H$_{37}$N$_5$O$_5$S; HCl; 0.50 CH$_2$Cl$_2$ requires C,54.79; H,6.07; N,10.83%.

The title compound of Preparation 73 was obtained from the corresponding nitrile precursor (Preparation 60) using the procedure described in Preparation 67. The title compounds of Preparations 68–72 and 74–79 were obtained from the corresponding nitrile precursors (Preparations 55–59 and 61–66 respectively), as in Preparation 67, but using the following modified work-up procedure.

The crude amidine hydrochloride, obtained directly from the amination step, was dissolved in water and this solution acidified to pH 2 with 1M hydrochloric acid, washed with ether, basified with 1M aqueous sodium hydroxide solution, saturated with sodium chloride and extracted with ethyl acetate. Evaporation under reduced pressure of the dried (MgSO$_4$) extract afforded the required amidine as its carbonate or hydrogen carbonate salt.

PREPARATION 68

4-Methyl-1-[N-(2-methyl-1,2,3,4-tetrahydroisoquinoline-6-sulphonyl)-3-amidino-(S)-phenylalanyl]-1,2,3,6-tetrahydropyridine-2(R)-carboxylic acid ethyl ester hydrogen carbonate Obtained from Preparation 55 as a white foam. Rf 0.50 (SS 24). m/e 568 (M+H)$^+$.

PREPARATION 69

4-Methyl-1-[N-(3-methyl-2,3,4,5-tetrahydro-1H-3-benzazepine-7-sulphonyl)-3-amidino-(S)-phenylalanyl]-1,2,3,6-tetrahydropyridine-2(R)-carboxylic acid ethyl ester hydrogen carbonate Obtained from Preparation 56 as a white solid. Rf 0.15 (SS 24). Found: C,57.68; H,6.78; N,10.85. C$_{30}$H$_{39}$N$_5$O$_3$S; H$_2$CO$_3$ requires C,57.84; H,6.42; N,10.88%.

PREPARATION 70

1-[N-(1(R,S)-Methoxymethyl-2-methyl-1,2,3,4-tetrahydroisoquinoline-7-sulphonyl)-3-amidino-(S)-phenylalanyl]-4-methyl-1,2,3,6-tetrahydropyridine-2(R)-carboxylic acid ethyl ester hydrogen carbonate Obtained from Preparation 57 as a white foam. Rf 0.40 (SS 24). Found: C,56.29; H,6.51; N,10.13. C$_{31}$H$_{41}$N$_5$O$_6$S; H$_2$CO$_3$; 0.50 H$_2$O requires C,56.29; E,6.49; N, 10.26%.

PREPARATION 71

1-{N-[1(R,S)-(N,N-Dimethylcarbamoylmethyl)-2-methyl-1,2,3,4-tetrahydroisoquinoline-7-sulphonyl]-3-amidino-(S)-phenylalanyl}-4-methyl-1,2,3,6-tetrahydropyridine-2(R)-carboxylic acid ethyl ester hydrogen carbonate Obtained from Preparation 58 as a white amorphous powder. Rf 0.32 (SS 24). Found: C,56.64; H,6.71; N,11.54. C$_{33}$H$_{44}$N$_6$O$_6$S; H$_2$CO$_3$; 0.30 CH$_3$CO$_2$CH$_2$CH$_3$ requires C,57.03; H,6.58; N,11.34%.

PREPARATION 72

4-Methyl-1-[N-(2,5-dimethyl-1,2,3,4-tetrahydroisoquinoline-8-sulphonyl)-3-amidino-(S)-phenylalanyl]-1,2,3,6-tetrahydropyridine-2(R)-carboxylic acid ethyl ester hydrogen carbonate Obtained from Preparation 59 as a white amorphous powder. Rf 0.68 (SS 24). Found: C,56.23; H,6.63; N,10.72. C$_{31}$H$_{41}$N$_5$O$_8$S; H$_2$CO$_3$; H$_2$O requires C,56.26; H,6.55; N,10.58%.

PREPARATION 73

4-Ethyl-1-[N-(2-methyl-1,2,3,4-tetrahydroisoquinoline-7-sulphonyl)-3-amidino-(S)-phenylalanyl]-1,2,3,6-tetrahydropyridine-2(R,S)-carboxylic acid ethyl ester hydrochloride Obtained from Preparation 60 as a colourless solid. Rf 0.21 (SS 25). Found: C,55.44; H,6.54; N,10.45. C$_{30}$H$_{39}$N$_5$O$_5$S; HCl; 0.50 CH$_2$Cl$_2$ requires C,55.21; H,6.19; N,10.55%.

PREPARATION 74

4-Methyl-1-{N-[3-(2-propyl)-2,3,4,5-tetrahydro-1H-3-benzazepine-7-sulphonyl]-3-amidino-(S)-phenylalanyl}-1,2,3,6-tetrahydropyridine-2(R)-carboxylic acid ethyl ester hydrogen carbonate Obtained from Preparation 61 as a white foam. Rf 0.34 (SS 24). m/e 610 (M+H)$^+$.

PREPARATION 75

1-{N-[3-3-Dimethylamino-1-propyl)-2,3,4,5-tetrahydro-1H-3-benzazepine-7-sulphonyl]-3-amidino-(S)-phenylalany}-4-methyl-1,2,3,6-tetrahydropyridine-2(R)-carboxylic acid ethyl ester hydrogen carbonate Obtained from Preparation 62 as a white foam. Rf 0.30 (SS 24). m/e 653 (M+H)$^+$.

PREPARATION 76

1-[N-(2-Benzyl-1,2,3,4-tetrahydroisoquinoline-7-sulphonyl)-3-amidino-(S)-phenylalanyl]-4-methyl-1,2,3,6-tetrahydropyridine-2(R)-carboxylic acid ethyl ester hydrogen carbonate Obtained from Preparation 63 as a white foam. Rf 0.49 (SS 24). m/e 644 (M+H)$^+$.

PREPARATION 77

4-Methyl-1-[N-(2-methyl-1,2,3,4-tetrahydroisoquinoline-7-sulphonyl)-3-amidino-(S)-phenylalanyl]-1,2,3,6-tetrahydropyridine-2(S)-carboxylic acid ethyl ester hydrogen carbonate Obtained from Preparation 64 as a white solid. Rf 0.13 (SS 9). m/e 568 (M+H)$^+$.

PREPARATION 78

4-Methyl-1-{N-[2-(2-propyl)-1,2,3,4-tetrahydroisoquinoline-7-sulphonyl]-3-amidino-(S)-phenylalanyl}-1,2,3,6-tetrahydropyridine-2(R)-carboxylic acid ethyl ester hydrogen carbonate Obtained from Preparation 65 as a foam. Rf 0.10 (SS 9). m/e 596 (M+H)$^+$.

PREPARATION 79

4(R)-Methyl-1-[N-(2-methyl-1,2,3,4-tetrahydroisoquinoline-7-sulphonyl)-3-amidino-(R,S)-phenylalanyl]piperidine-2(R)-carboxylic acid ethyl ester carbonate Obtained from Preparation 66 as a white amorphous solid by precipitation from acetonitrile using ether. Rf 0.10 (SS 3). Found: C,58.05; H,6.59; N,11.35. C$_{29}$H$_{39}$N$_5$O$_5$; 0.50 H$_2$CO$_3$; 0.50 H$_2$O requires C,58.11; H,6.78; N,11.48%.

PREPARATION 80

4-Methyl-1-[N-(2-methyl-1,2,3,4-tetrahydroisoquinoline-7-sulphonyl)-3-(2-amidino-4-pyridyl-(S)-alanyl]-1,2,3,6-tetrahydropyridine-2(R)-carboxylic acid ethyl ester hydrochloride Sodium metal (30 mg, 1.3 mmol) was added to a stirred solution of 4-methyl-1-[N-(2-methyl-1,2,3,4-tetrahydroisoquinoline-7-sulphonyl)-3-(2-cyano-4-pyridyl)-(S)-alanyl]-1,2,3,6-tetrahydropyridine-2(R)-carboxylic acid ethyl ester (Preparation 54; 243 mg, 0.44 mmol) in ethanol (4 ml) at room temperature. After 1 hour, ammonium chloride (140 mg, 2.6 mmol) was added and the resulting mixture stirred for 18 hours and then filtered. Evaporation under reduced pressure of the filtrate followed by purification of the residue by chromatography on silica gel, using dichloromethane:methanol:0.880 aqueous ammonia solution (90:10:1) as eluent, furnished the title compound (176 mg) as a foam. Rf 0.21 (SS 13). Found: C,55.64; H,6.31; N,13.47. $C_{28}H_{36}N_6O_5S$; HCl requires C,55.56; H,6.16; N,13.88%.

PREPARATION 81

4-Methyl-1-[N-(1,2,3,4-tetrahydroisoquinoline-7-sulphonyl)-3-amidino-(S)-phenylalanyl]-1,2,3,6-tetrahydropyridine-2(R,S)-carboxylic acid ethyl ester hydrogen carbonate A stirred, ice-cooled solution of 4-methyl-1-[N-(2-trifluoroacetyl-1,2,3,4-tetrahydroiso-quinoline-7-sulphonyl)-3-cyano-(S)-phenylalanyl]-1,2,3,6-tetrahydropyridine-2(R,S)-carboxylic acid ethyl ester (Preparation 43; 504 mg, 0.8 mmol) in dry ethanol (6 ml) was saturated with hydrogen chloride, refrigerated for 20 hours and then evaporated under reduced pressure. The residue was dissolved in dry ethanol (10 ml), the solution evaporated under reduced pressure and the resulting white foam dissolved in dry ethanol (25 ml). This solution was stirred under reflux whilst saturating with ammonia and, after 4 hours of heating under reflux, was evaporated under reduced pressure. The residue was dissolved in water and the solution washed with ether, basified with 1M aqueous sodium hydroxide solution and extracted with dichloromethane. The extract was washed with saturated brine, dried ($MgSO_4$) and evaporated under reduced pressure to provide the title compound (435 mg) as a white solid. Rf 0.15 (SS 13). Found: C,54.73; H,6.07; N,11.04. $C_{28}H_{35}N_5O_5S$; $H_2CO_3$; $H_2O$ requires C,54.96; H,6.20; N,11.05%.

Biological activity

The following Table illustrates the in vitro inhibitory activities against thrombin, trypsin and plasmin for a range of the compounds of the invention.

TABLE

| | Ki (M) | | |
|---|---|---|---|
| EXAMPLE | THROMBIN | TRYPSIN | PLASMIN |
| 2 | $3.9 \times 10^{-9}$ | $5.7 \times 10^{-8}$ | $6.1 \times 10^{-6}$ |
| 5 | $2.2 \times 10^{-9}$ | $5.4 \times 10^{-8}$ | $6.0 \times 10^{-6}$ |
| 8 | $6.4 \times 10^{-9}$ | $4.0 \times 10^{-8}$ | $1.8 \times 10^{-6}$ |
| 10 | $1.0 \times 10^{-9}$ | $4.8 \times 10^{-8}$ | $1.8 \times 10^{-7}$ |
| 13 | $4.0 \times 10^{-9}$ | $4.9 \times 10^{-8}$ | $1.2 \times 10^{-5}$ |
| 15 | $7.8 \times 10^{-8}$ | $3.2 \times 10^{-7}$ | $1.4 \times 10^{-5}$ |

Safety profile

Several compounds of the invention have been tested at multiple doses of up to 30 mg/kg i.v. in mouse and up to 20 mg/kg i.v. in rat without showing any sign of adverse toxicity.

We claim:

1. A compound of formula (I)

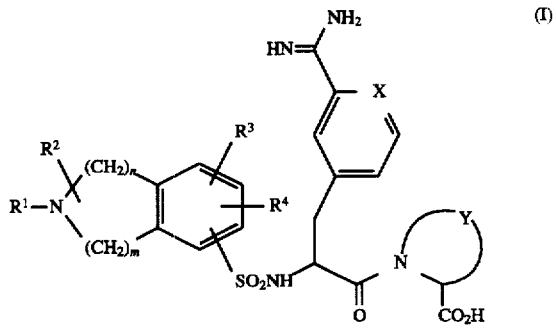

or a pharmaceutically acceptable salt thereof, or a pharmaceutically acceptable solvate of either said compound or said salt, wherein X is CH or N;

Y is optionally monounsaturated $C_3$-$C_5$ alkylene optionally substituted with $C_1$-$C_4$ alkyl or methylene;

$R^1$ is H; $C_1$-$C_4$ alkyl optionally substituted with $C_1$-$C_4$ alkoxy, OH, $NR^5R^6$, $CONR^5R^6$, $C_3$-$C_6$ cycloalkyl or aryl; or $C_3$-$C_6$ alkenyl;

$R^2$ is H; $C_1$-$C_4$ alkyl optionally substituted with $C_1$-$C_4$ alkoxy, OH, $NR^5R^6$, $CONR^5R^6$, $C_3$-$C_6$ cycloalkyl or aryl; or $CONR^5R^6$;

$R^3$ and $R^4$ are each independently selected from H; $C_1$-$C_4$ alkyl optionally substituted with $NR^5R^6$; $C_1$-$C_4$ alkoxy; halo; $CONR^5R^6$ and aryl;

$R^5$ and $R^6$ are each independently selected from H and $C_1$-$C_4$ alkyl;

m is 1;

n is 2.

2. A compound according to claim 1 wherein the preferred stereoisomer is of formula

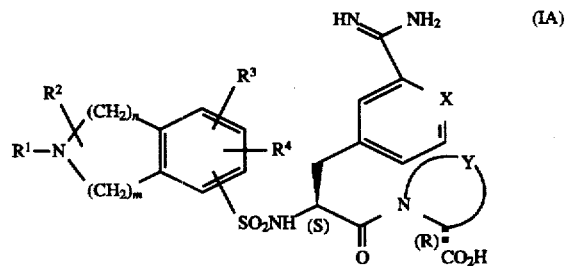

wherein m is 1 and n is 2.

3. A compound according to claim 2 wherein Y is monounsaturated $C_3$-$C_5$ alkylene substituted with methyl or ethyl; $R^1$ is H; or $C_1$-$C_4$ alkyl optionally substituted with $NR^5R^6$ or phenyl; $R^2$ is H; $C_1$-$C_2$ alkyl substituted with $C_1$-$C_4$ alkoxy, $NR^5R^6$ or $CONR^5R^6$; or $CONR^5R^6$; $R^3$ and $R^4$ are each independently selected from H, methyl, $CH_2NR^5R^6$, methoxy, $CONR^5R^6$ and phenyl; $R^5$ and $R^6$ are each independently selected from H and methyl.

4. A compound according to claim 3 of formula (IB):

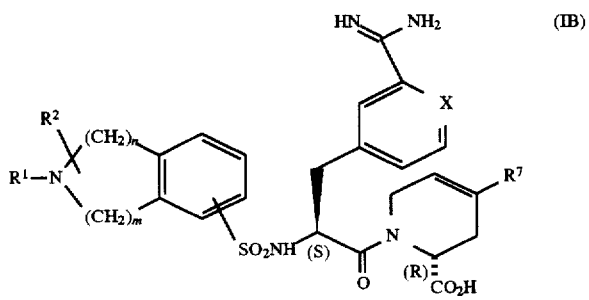

wherein $R^1$ is methyl, ethyl, 2-propyl, 3-dimethylamino-1-propyl or benzyl; $R^2$ is H, $CH_2OCH_3$ or $CH_2CON(CH_3)_2$; $R_7$ is methyl or ethyl; m is 1; and n is 2.

5. A compound according to claim 4 wherein the compound of formula (IB) is 4-methyl-1-(N-(2-methyl-1,2,3,4-tetrahydroisoquinoline-7-sulphonyl)-3-amidino-(S)-phenylalanyl)-1,2,3,6-tetrahydropyridine-2R)-carboxylic acid; a pharmaceutically acceptable salt thereof, and a pharmaceutically acceptable solvate of either said compound or said salt.

6. A pharmaceutical composition comprising a compound of claim 1 together with a pharmaceutically acceptable diluent or carrier.

7. A compound of formula (II):

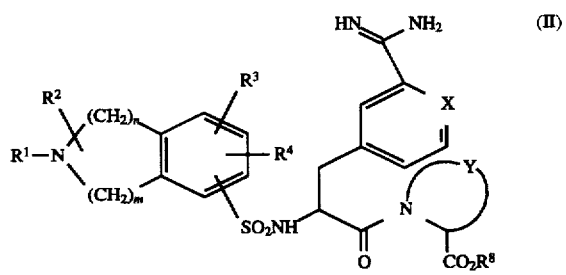

wherein

X is CH or N;

Y is optionally monounsaturated $C_3$-$C_5$ alkylene optionally substituted with $C_1$-$C_4$ alkyl or methylene;

$R^1$ is H; $C_1$-$C_4$ alkyl optionally substituted with $C_1$-$C_4$ alkoxy, OH, $NR^5R^6$,
$CONR^5R^6$, $C_3$-$C_6$ cycloalkyl or aryl; or $C_3$-$C_6$ alkenyl;

$R^2$ is H; $C_1$-$C_4$ alkyl optionally substituted with $C_1$-$C_4$ alkoxy, OH, $NR^5R^6$, $CONR^5R^6$,
$C_3$-$C_6$ cycloalkyl or aryl; or $CONR^5R^6$;

$R^3$ and $R^4$ are each independently selected from H; $C_1$-$C_4$ alkyl optionally substituted with $NR^5R^6$;
$C_1$-$C_4$ alkoxy; halo; $CONR^5R^6$ and aryl;

$R^8$ is $C_1$-$C_3$ alkyl;

$R^5$ and $R^6$ are each independently selected from H and $C_1$-$C_4$ alkyl;

m is 1; and n is 2.

8. A compound according to claim 7 wherein $R^8$ is methyl or ethyl.

9. A method of treating a mammal in need of therapeutic treatment comprising administering to said mammal an effective amount of a compound of claim 1 or a pharmaceutical composition thereof wherein said need results from deep vein thrombosis (DVT) after surgery, major medical illness, paralysis, malignancy, prolonged immobilization trauma, application of lower limb plaster casts, or fractures of the lower limbs or pelvis; recurrent DVT; DVT during pregnancy when there is a previous history thereof; reocclusion following thrombolytic therapy; chronic arterial obstruction; peripheral vascular disease; acute myocardial infarction; unstable angina; atrial fibrillation; thrombotic stroke; transient ischaemic attacks; disseminated intravascular coagulation; coagulation in extra-corporeal circuits; occlusion of arterio-venous shunts and blood vessel grafts (including coronary artery by-pass grafts); restenosis and occlusion following angioplasty; neurodegenerative disorders; inflammatory disorders; or scarring.

10. A process for the preparation of a compound of formula (I):

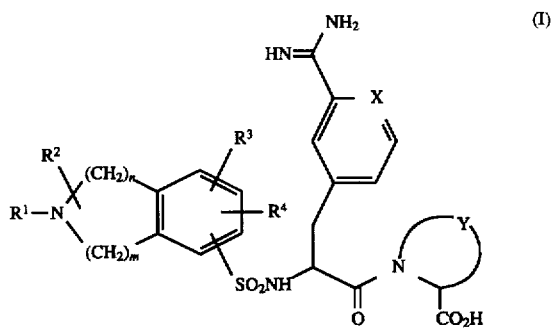

or a pharmaceutically acceptable salt thereof, or a pharmaceutically acceptable solvate of either said compound or said salt wherein X is CH or N;

Y is optionally monounsaturated $C_3$-$C_5$ alkylene optionally substituted with $C_1$-$C_4$ alkyl or methylene;

$R^1$ is H; $C_1$-$C_4$ alkyl optionally substituted with $C_1$-$C_4$ alkoxy, OH, $NR^5R^6$,
$CONR^5R^6$, $C_3$-$C_6$ cycloalkyl or aryl; or $C_3$-$C_6$ alkenyl;

$R^2$ is H; $C_1$-$C_4$ alkyl optionally substituted with $C_1$-$C_4$ alkoxy, OH, $NR^5R^6$,
$CONR^5R^6$, $C_3$-$C_6$ alkenyl or aryl; or $CONR^5R^6$;

$R^3$ and $R^4$ are each independently selected from H; $C_1$-$C_4$ alkyl optionally substituted with $NR^5R^6$; $C_1$-$C_4$ alkoxy; halo; $CONR^5R^6$ and aryl;

$R^5$ and $R^6$ are each independently selected from H and $C_1$-$C_4$ alkyl;

m is 1; and n is 2;

which comprises acid-or base-catalyzed hydrolysis of a compound of formula (II):

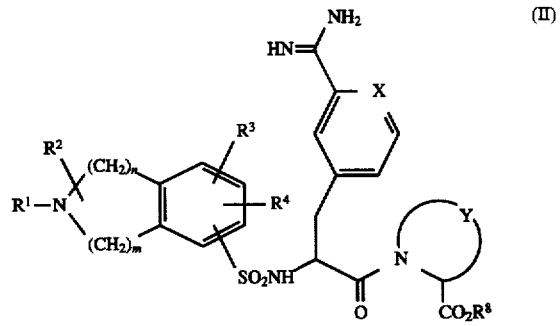

wherein $R^8$ is $C_1$-$C_3$ alkyl, and X, Y, $R^1$, $R^2$, $R^3$ and $R^4$ are as previously defined in this claim; m is 1; and n is 2; followed by optional formation of a pharmaceutically acceptable salt of the required product or a pharmaceutically acceptable solvate of either said compound or said salt.

11. A process according to claim 10 which is base-catalysed in aqueous medium, optionally in the presence of a cosolvent, at from about room temperature to about 100° C.

12. A process according to claim 11 wherein the base is an alkali metal hydroxide.

13. A process according to claim 12 wherein the base is sodium hydroxide, the cosolvent is 1,4-dioxan and the reaction is conducted at about room temperature.

14. A process according to claim 13 wherein $R^8$ is methyl or ethyl.

15. A process according to claim 14 wherein the preferred steroisomer of a compound of formula (I) produced from the corresponding stereoisomer of a compound of formula (II) is of formula (IA):

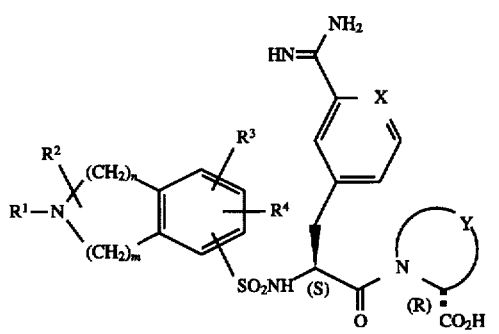

wherein m is 1 and n is 2.

16. A process according to claim 15 wherein Y is monounsaturated $C_3$-$C_5$ alkylene substituted with methyl or ethyl;

$R^1$ is H; or $C_1$-$C_4$ alkyl optionally substituted with $NR^5R^6$ or phenyl;

$R^2$ is H; $C_1$-$C_2$ alkyl substituted with $C_1$-$C_4$ alkoxy, $NR^5R^6$ or $CONR^5R^6$;

$R^3$ and $R^4$ are each independently selected from H, methyl, $CH_2NR^5R^6$, methoxy, $CONR^5R^6$ and phenyl; and $R^5$ and $R^6$ are each independently selected from H and methyl.

17. A process according to claim 16 wherein the compound produced is of formula (IB):

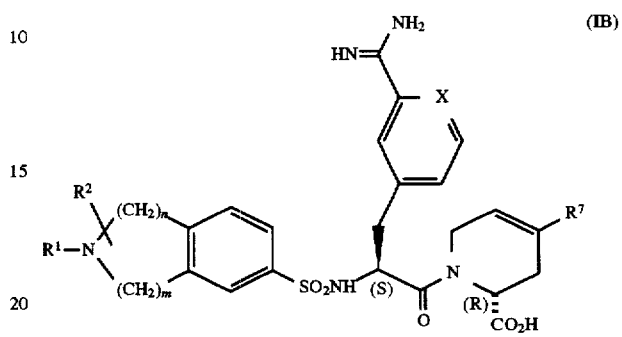

wherein $R^1$ is methyl, ethyl, 2-propyl, 3-dimethylamino-1-propyl or benzyl; $R^2$ is H, $CH_2OCH_3$ or $CH_2CON(CH_3)_2$; $R^7$ is methyl or ethyl; m is 1; and n is 2.

18. A process according to claim 17 wherein the compound of formula (IB) produced is 4-methyl-1-(N-(2-methyl-1,2,3,4-tetrahydroisoquinoline-7-sulphonyl)-3-amidino-(S)-phenylalanyl)-1,2,3,6-tetrahydropyridine-2(R)-carboxylic acid; a pharmaceutically acceptable salt thereof, and a pharmaceutically acceptable solvate of either said compound or said salt.

* * * * *